United States Patent
Wagner

(10) Patent No.: US 7,038,046 B2
(45) Date of Patent: May 2, 2006

(54) TRIAZINE DERIVATIVES AND THEIR USE AS SUNSCREENS

(75) Inventor: Barbara Wagner, Lörrach (DE)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 170 days.

(21) Appl. No.: 10/486,761

(22) PCT Filed: Aug. 8, 2002

(86) PCT No.: PCT/EP02/08888

§ 371 (c)(1), (2), (4) Date: Feb. 11, 2004

(87) PCT Pub. No.: WO03/016289

PCT Pub. Date: Feb. 27, 2003

(65) Prior Publication Data

US 2004/0242579 A1    Dec. 2, 2004

(30) Foreign Application Priority Data

Aug. 17, 2001 (EP) ............................. 01810796
Sep. 14, 2001 (CH) ............................. 16991/01

(51) Int. Cl.
C07D 251/52 (2006.01)
C07D 251/54 (2006.01)
C07D 251/48 (2006.01)
A61K 7/42 (2006.01)

(52) U.S. Cl. .................... 544/196; 544/204; 424/70.1; 424/70.9

(58) Field of Classification Search ................. 544/196, 544/204; 424/70.1, 70.9
See application file for complete search history.

(56) References Cited

U.S. PATENT DOCUMENTS 5,520,906 A    5/1996    Stein et al. ................ 424/59
5,928,630 A    7/1999    Richard et al. ............. 424/59

FOREIGN PATENT DOCUMENTS

DE             4105923            8/1992

*Primary Examiner*—Venkataraman Balasubramanian
(74) *Attorney, Agent, or Firm*—Kevin T. Mansfield

(57) ABSTRACT

There are described triazine derivatives of formula (1), wherein $R_1$ is an unsubstituted or mono- or poly-hydroxy-, $C_1$–$C_{18}$ alkyl-, $C_1$–$C_{18}$ alkoxy-, amino-, $C_1$–$C_5$ monoalkylamino- or di-$C_1$–$C_5$ alkylamino-substituted $C_1$–$C_{18}$ alkyl, $C_2$–$C_{18}$ alkenyl, $C_6$–$C_{10}$ aryl or $C_6$–$C_{10}$ heteroaryl radical; unsubstituted or $C_1$–$C_5$ alkyl-substituted $C_5$–$C_7$ cycloalkyl or $C_5$–$C_7$ cycloalkenyl; —OR'; or —NR'R"; $R_2$ is hydrogen; an unsubstituted or mono- or poly-hydroxy-, $C_1$–$C_{18}$ alkoxy-, cyano-, amino-, $C_1$–$C_5$ monoalkylamino- or di-$C_1$–$C_5$ alkylamino-substituted $C_1$–$C_{18}$ alkyl, $C_2$–$C_{18}$ alkenyl; $C_6$–$C_{10}$ aryl or $C_6$–$C_{10}$ heteroaryl radical; —OR'; or —NR'R"; or $R_1$ and $R_2$ together form a 5- to 7-membered carbocyclic or heterocyclic ring; A is $C_1$–$C_5$ alkyl; an unsubstituted or hydroxy-, $C_1$–$C_{18}$ alkyl- or $C_1$–$C_{18}$ alkoxy-substituted $C_6$–$C_{10}$ aryl or heteroaryl radical; or a radical of formula (1a); R' and R" are each independently of the other hydrogen; unsubstituted or mono- or poly-hydroxy-, halo-, $C_1$–$C_{18}$ alkyl-, $C_1$–$C_{18}$ alkoxy-, amino- or quaternary ammonium group-substituted $C_1$–$C_{18}$ alkyl, $C_5$–$C_7$ cycloalkyl or phenyl; $R_3$ is hydrogen; or $C_1$–$C_6$ alkyl; and n is 0 or 1. The compounds according to the invention are suitable especially as sun protective agents in cosmetic, pharmaceutical and veterinary medicine preparations

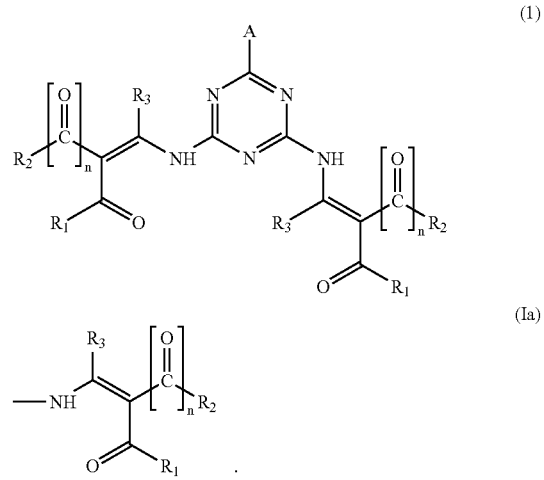

12 Claims, No Drawings

TRIAZINE DERIVATIVES AND THEIR USE AS SUNSCREENS

The present invention relates to novel triazine derivatives, to a process for the preparation of such compounds and to the use of such compounds for cosmetic preparations.

The novel triazine derivatives correspond to the formula

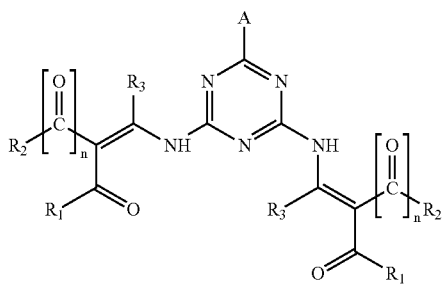

(1)

wherein
  $R_1$ is a $C_1$–$C_{18}$alkyl, $C_2$–$C_{18}$alkenyl, $C_6$–$C_{10}$aryl or $C_6$–$C_{10}$heteroaryl radical each unsubstituted or mono- or poly-substituted by hydroxy, $C_1$–$C_{18}$alkyl, $C_1$–$C_{18}$alkoxy, amino, $C_1$–$C_5$mono-alkylamino or by di-$C_1$–$C_5$alkylamino; $C_5$–$C_7$cycloalkyl or $C_5$–$C_7$cycloalkenyl each unsubstituted or substituted by $C_1$–$C_5$alkyl; —OR'; or —NR'R";
  $R_2$ is hydrogen; a $C_1$–$C_{18}$alkyl, $C_2$–$C_{18}$alkenyl; $C_6$–$C_{10}$aryl or $C_6$–$C_{10}$heteroaryl radical each unsubstituted or mono- or poly-substituted by hydroxy, $C_1$–$C_{18}$alkyl, $C_1$–$C_{18}$alkoxy, cyano, amino, $C_1$–$C_5$monoalkylamino or by di-$C_1$–$C_5$alkylamino; —OR'; or —NR'R"; or
  $R_1$ and $R_2$ together form a 5- to 7-membered carbocyclic or heterocyclic ring;
  A is $C_1$–$C_5$alkyl; an unsubstituted or hydroxy-, $C_1$–$C_{18}$alkyl- or $C_1$–$C_{18}$alkoxy-substituted $C_6$–$C_{10}$aryl or $C_6$–$C_{10}$heteroaryl radical; or a radical of formula (1a)

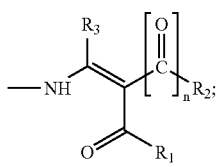

R' and R" are each independently of the other hydrogen; unsubstituted or mono- or poly-hydroxy-, halo-, $C_1$–$C_{18}$alkyl-, $C_1$–$C_{18}$alkoxy-, amino- or quaternary ammonium group-substituted $C_1$–$C_{18}$alkyl, $C_5$–$C_7$cycloalkyl or phenyl;
  $R_3$ is hydrogen; or $C_1$–$C_6$alkyl; and
  n is 0 or 1.

$C_1$–$C_{18}$Alkyl denotes straight-chain or branched hydrocarbon radicals, for example methyl, ethyl, propyl, isopropyl, n-butyl, sec-butyl, isobutyl, tert-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetra-methylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylundecyl, dodecyl, tridecyl, tetradecyl, pentadecyl or hexadecyl or octadecyl.

$C_1$–$C_{18}$Alkoxy denotes straight-chain or branched radicals, for example methoxy, ethoxy, n-propoxy, isopropoxy, n-butoxy, sec-butoxy, tert-butoxy, amyloxy, isoamyloxy or tert-amyloxy, n-hexyloxy, 1-methylhexyloxy, n-heptyloxy, isoheptyloxy, 1,1,3,3-tetramethyl-butoxy, 1-methylheptyloxy, 3-methylheptyloxy, n-octyloxy, 2-ethylhexyloxy, 1,1,3-tri-methylhexyloxy, 1,1,3,3-tetramethylpentyloxy, nonyloxy, decyloxy, undecyloxy, 1-methylundecyloxy, dodecyloxy, tridecyloxy, tetradecyloxy, pentadecyloxy, hexadecyloxy or octadecyloxy.

$C_2$–$C_{18}$Alkenyl is, for example, allyl, methallyl, isopropenyl, 2-butenyl, 3-butenyl, isobutenyl, n-penta-2,4-dienyl, 3-methyl-but-2-enyl, n-oct-2-enyl, n-dodec-2-enyl, isododecenyl, n-dodec-2-enyl or n-octadec-4-enyl.

$C_6$–$C_{18}$Aryl is, for example, phenyl or naphthyl.

A heterocyclic ring is a heteroaromatic system containing at least one oxygen, sulfur and/or nitrogen hetero atom in the ring structure. Preferred heteroaryl groups preferably contain from 2 to 15 carbon atoms.

Examples of mono- or di-$C_1$–$C_5$alkylamino are methylamino, ethylamino, propylamino, n-butylamino, sec-butylamino, tert-butylamino, pentylamino, dimethylamino, diethylamino, dipropylamino, dibutylamino and methylethylamino.

Preference is given to triazine derivatives of formula (1) wherein
  $R_1$ and $R_2$ are each independently of the other $C_1$–$C_{18}$alkyl or phenyl each unsubstituted or substituted by $C_1$–$C_5$alkyl, hydroxy or by $C_1$–$C_5$alkoxy; —OR'; or —NR'R"; or $R_1$ and $R_2$ together form a 5- to 7-membered carbocyclic or heterocyclic ring.

More especially preferred are compounds of formula (1) wherein
  $R_1$ is $C_1$–$C_5$alkyl; $C_1$–$C_5$alkoxy; or unsubstituted or $C_1$–$C_5$alkyl-, hydroxy- or $C_1$–$C_5$alkoxy-substituted phenyl.

Also preferred are compounds of formula (1) wherein
  $R_2$ is hydrogen; $C_1$–$C_5$alkyl; $C_1$–$C_5$alkoxy; unsubstituted or hydroxy-, $C_1$–$C_5$alkyl- or $C_1$–$C_5$-alkoxy-substituted phenyl; and
  n is 1.

Preference is also given to compounds of formula (1) wherein
  $R_1$ and $R_2$ together are a —$(CH_2)_{2-5}$— radical that is not further substituted or is substituted by one or more $C_1$–$C_5$alkyl and is uninterrupted or interrupted by one or two —O— and/or —NH— groups and/or

Very special preference is given to compounds of formula (1) wherein
  $R_1$ and R together are a

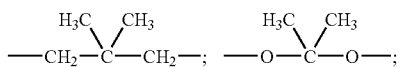

-continued

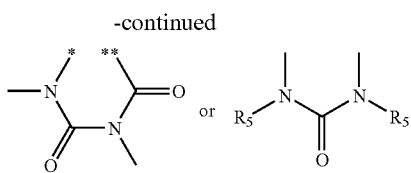

radical;
R₅ is hydrogen; or $C_1$–$C_5$alkyl.

A in formula (1) is especially amino; phenyl; or $C_1$–$C_5$alkoxyphenyl.

$R_3$ in formula (1) is especially hydrogen.

Special preference is given to compounds of formula (1) wherein $R_1$ and $R_2$ are $C_1$–$C_5$alkyl.

Examples of compounds according to the invention are listed in Table 1 below:

TABLE 1

| Compound of formula | $R_1$ | $R_2$ |
|---|---|---|
| (2) | *–O–C(CH₃)₃ | **–C(O)–O–C(CH₃)₃ |
| (3) | *–O–CH₂CH₃ | **–C(O)–O–CH₂CH₃ |
| (4) | *–O–CH(CH₃)₂ | **–C(O)–O–CH(CH₃)₂ |
| (5) | *–O–CH₃ | **–C(O)–O–CH₃ |
| (6) | *–phenyl | **–C₆H₄–OH |
| (7) | *–phenyl | **–C(O)–phenyl |
| (8) | *–C₆H₄–O–Me | **–C(O)–C₆H₄–C(CH₃)₃ |
| (9) | | *–CH₂CH₂–C₆H₄–** |
| (10) | | **–C₆H₄–CH₂–* |

(A is methyl, phenyl, amino, p-methoxyphenyl)

TABLE 1-continued
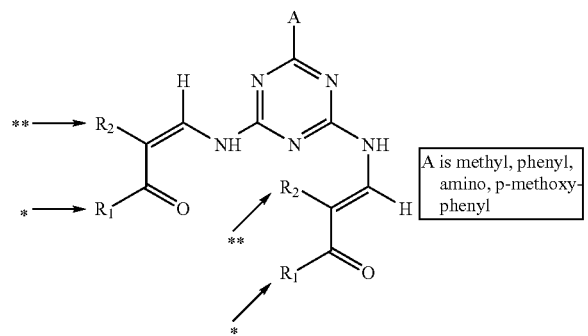
A is methyl, phenyl, amino, p-methoxyphenyl
| Compound of formula | R₁ | R₂ |
|---|---|---|
| (11) | *—O—CH₃ |  |
| (12) | 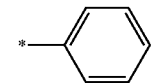 | H |
| (13) | 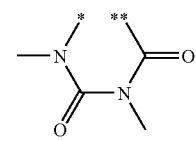 | |
| (14) | 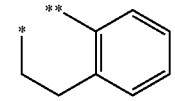 | |
| (15) | 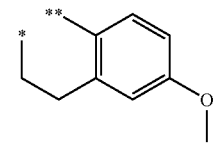 | |
| (16) | 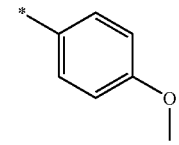 | H |
| (17) | *—CH₃ | 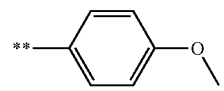 |
| (18) | *—O—C₂H₅ | 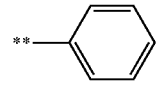 |
| (19) | 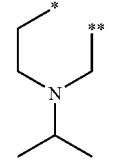 | |
| (20) | 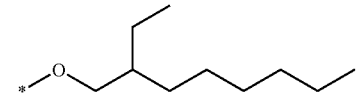 | **—CN |

TABLE 1-continued
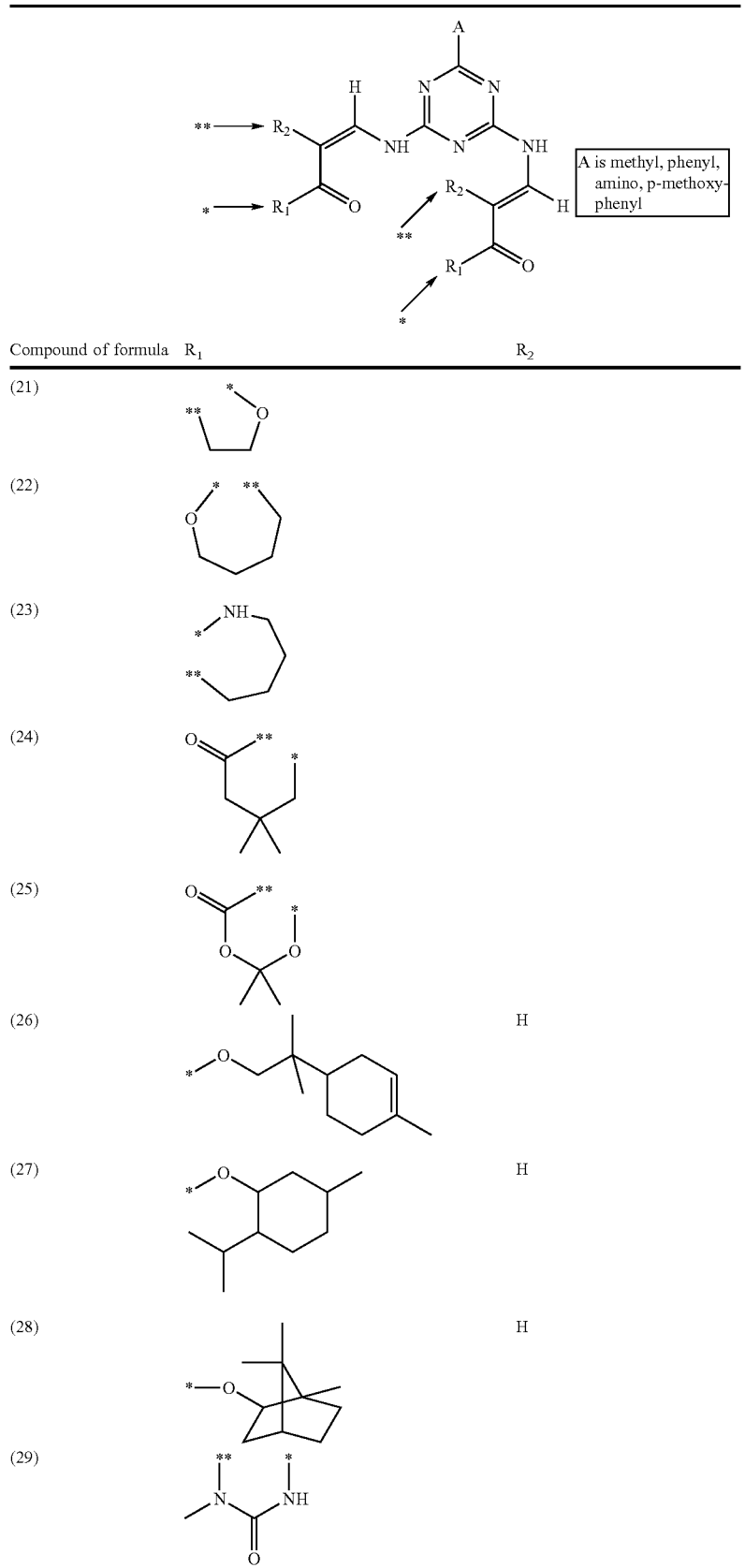
A is methyl, phenyl, amino, p-methoxy-phenyl
| Compound of formula | R₁ | R₂ |
|---|---|---|
| (21) | | |
| (22) | | |
| (23) | | |
| (24) | | |
| (25) | | |
| (26) | | H |
| (27) | | H |
| (28) | | H |
| (29) | | |

TABLE 1-continued
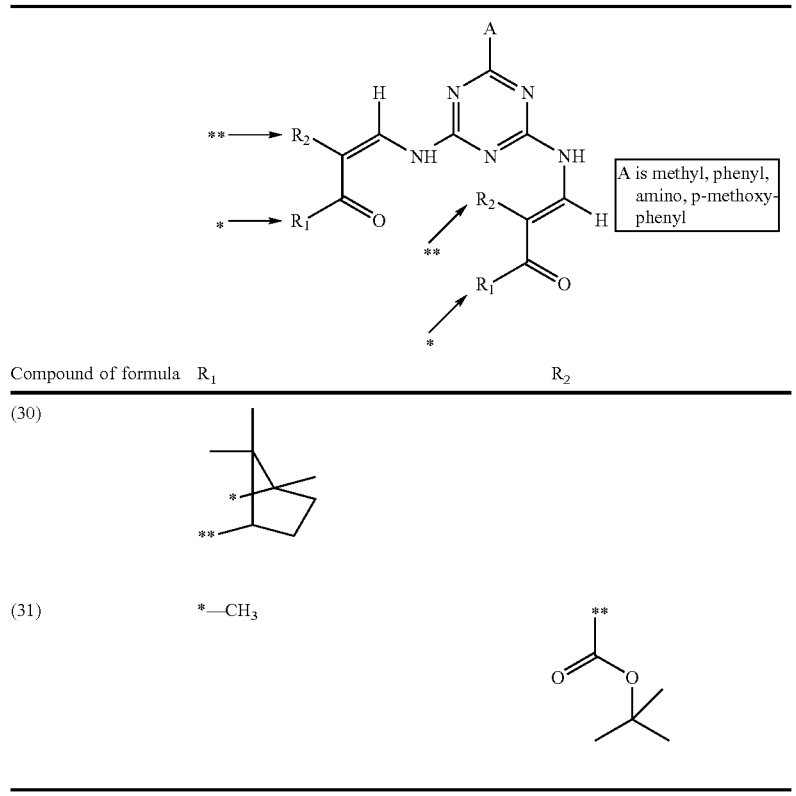
| Compound of formula | $R_1$ | $R_2$ |
|---|---|---|
| (30) | | |
| (31) | *—CH$_3$ | |
Especially preferred are compounds of formulae
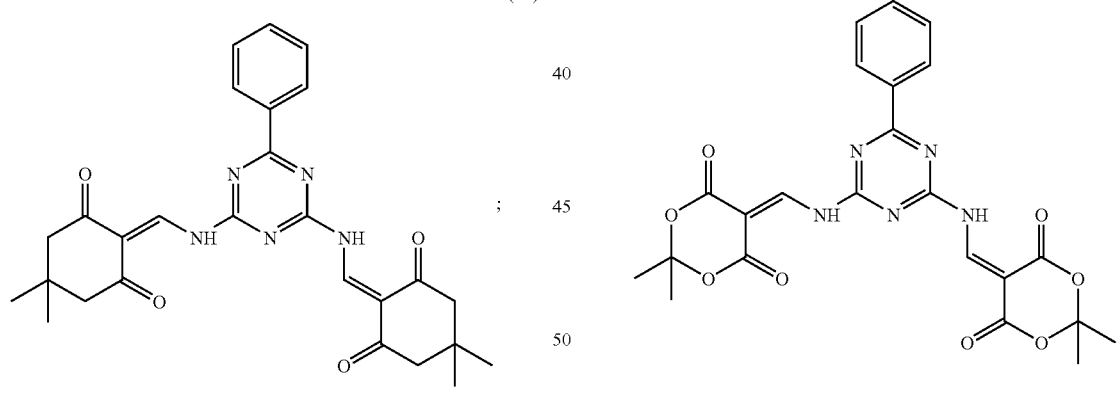
and
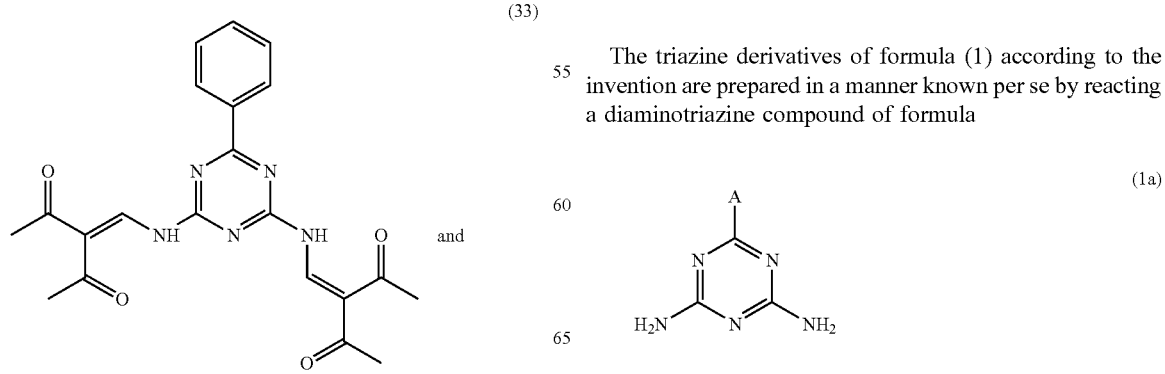
The triazine derivatives of formula (1) according to the invention are prepared in a manner known per se by reacting a diaminotriazine compound of formula
(1a)

with a compound of formula

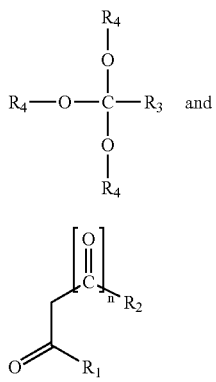

wherein
R₄ is $C_1$–$C_5$alkyl and $R_1$, $R_2$, $R_3$, A and n are as defined for formula (1), to form a compound of formula (1).

The reaction is carried out in the presence of an acid, with or without the addition of one or more solvents at a reaction temperature of from 0 to 200° C.

Generally from 0.8 to 2.0 mol of the compound of formula (1b) and from 0.8 to 2.0 mol of a compound of formula (1c) are used per free amino group of compound (1a).

The reaction is preferably carried out in DMSO, N-methylpyrrolidone, DMF or DMA. It is also possible, however, to use protic solvents, such as ethanol, methanol, isobutanol or isopropanol. The reaction can also be carried out in an aliphatic or aromatic solvent, such as hexane, toluene or xylene. It is also possible to use ethers, such as diethyl ether and tetrahydrofuran, or halogenated solvents, such as chloroform or dichloromethane.

The reaction is preferably carried out as a one-pot reaction. The individual reactants may, however, be added in any desired order. For example, the catalyst may be present from the beginning or may be introduced only later. It is also possible first to start the reaction between (1b) and (1c) in the presence of the catalyst and only later to add the triazine compound of formula (1a). It is equally possible first to react the compound of formula (1a) with the compound of formula (1b) in the presence of a catalyst and to add (1c) later. The reaction can be carried out at a temperature of from 0 to 200° C., preferably at from 20 to 100° C. and especially from 50 to 80° C.

The reaction times are dependent upon the reaction temperature. Within the preferred temperature range, the reactions are generally completed within from 1 to 6 hours. At low temperatures, the reaction time increases considerably and may be 48 hours or more.

As catalysts there are used organic and inorganic Brönstedt or Lewis acids or mixtures thereof. Examples of typical acids are phosphoric acid, trifluoroacetic acid, oxalic acid, methanesulfonic acid, toluenesulfonic acid, phenylsulfonic acid and trifluoromethanesulfonic acid. Also effective are acid anhydrides, for example trifluoromethanesulfonic anhydride, methanesulfonic anhydride and acetic anhydride. Preference is given, however, to the use of Lewis acids, such as phosphorus oxychloride, copper chlorides, zinc chloride, lanthanum chloride, chromium chlorides, iron chlorides, aluminium chloride, titanium chlorides, germanium chloride, and hydrates thereof. It is also possible to use acidic ion exchangers.

The product is isolated according to conventional techniques, such as filtration, centrifugation, phase separation and liquid extraction. The products are purified, inter alia, by recrystallisation from a solvent or from a solvent mixture, preference being given to solvents or solvent mixtures containing alcohols. Purification can also be carried out by chromatographic methods and by distillation.

The compounds of formula (1) according to the invention are suitable especially as UV filters, that is to say to protect organic materials that are sensitive to ultraviolet light, especially human and animal skin and hair, against the damaging effect of UV radiation. The compounds are accordingly suitable as light-protective agents in cosmetic, pharmaceutical and veterinary medicine preparations. The compounds can be used either in the dissolved state or in the micronised state.

The invention accordingly relates also to a cosmetic preparation comprising at least one compound of formula (1), and to cosmetically tolerable carriers or adjuvants.

In addition to the UV absorber according to the invention, the cosmetic preparation may also comprise one or more further UV protective substances of the following substance classes:

1. p-aminobenzoic acid derivatives, for example 4-dimethylaminobenzoic acid 2-ethylhexyl ester;
2. salicylic acid derivatives, for example salicylic acid 2-ethylhexyl ester;
3. benzophenone derivatives, for example 2-hydroxy-4-methoxybenzophenone and its 5-sulfonic acid derivative;
4. dibenzoylmethane derivatives, for example 1-(4-tert-butylphenyl)-3-(4-methoxyphenyl)-propane-1,3-dione;
5. diphenylacrylates, for example 2-ethylhexyl 2-cyano-3,3-diphenylacrylate, and 3-(benzofuranyl) 2-cyanoacrylate;
6. 3-imidazol-4-ylacrylic acid and esters;
7. benzofuran derivatives, especially 2-(p-aminophenyl) benzofuran derivatives, described in EP-A-582 189, U.S. Pat. No. 5,338,539, U.S. Pat. No. 5,518,713 and EP-A-613 893;
8. polymeric UV absorbers, for example the benzylidene malonate derivatives described in EP-A-709 080;
9. cinnamic acid derivatives, for example the 4-methoxycinnamic acid 2-ethylhexyl ester and isoamyl ester or cinnamic acid derivatives disclosed in U.S. Pat. No. 5,601,811 and WO 97/00851;
10. camphor derivatives, for example 3-(4'-methyl) benzylidene-bornan-2-one, 3-benzylidenebornan-2-one, N-[2(and 4)-2-oxyborn-3-ylidene-methyl)-benzyl] acrylamide polymer, 3-(4'-trimethylammonium)-benzylidene-bornan-2-one methyl sulfate, 3,3'-(1,4-phenylenedimethine)-bis(7,7-dimethyl-2-oxo-bicyclo [2.2.1]heptane-1-methanesulfonic acid) and salts, 3-(4'-sulfo)benzylidene-bornan-2-one and salts; camphorbenzalkonium methosulfate;
11. hydroxyphenyltriazine compounds, for example 2-(4'-methoxyphenyl)-4,6-bis(2'-hydroxy-4'-n-octyloxyphenyl)-1,3,5-triazine; 2,4-bis{[4-(3-(2-propyloxy)-2-hydroxy-propyloxy)-2-hydroxy]-phenyl}-6-(4-methoxyphenyl)-1,3,5-triazine; 2,4-bis{[4-(2-ethylhexyloxy)-2-hydroxy]-phenyl}-6-[4-(2-methoxyethyl-carboxyl)-phenylamino]-1,3,5-triazine; 2,4-bis{[4-(tris(trimethylsilyloxy-silylpropyloxy)-2-hydroxy]-phenyl}-6-(4-methoxyphenyl)-1,3,5-triazine; 2,4-bis{[4-(2"-methylpropenyloxy)-2-hydroxy]-phenyl}-6-(4-methoxyphenyl)-1,3,5-triazine; 2,4-bis{[4-(1',1',1', 3',5',5',5'-heptamethyltrisilyl-2"-methyl-propyloxy)-2-hydroxy]-phenyl}-6-(4-methoxyphenyl)-1,3,5-triazine; 2,4-bis{[4-(3-(2-propyloxy)-2-hydroxy-propyloxy)-2-hydroxy]-phenyl[-6-}4-ethyicarboxy)-phenylamino]-1,3, 5-triazine;

12. benzotriazole compounds, for example 2,2′-methylene-bis(6-(2H-benzotriazol-2-yl)-4-(1,1,3,3-tetramethylbutyl)-phenol

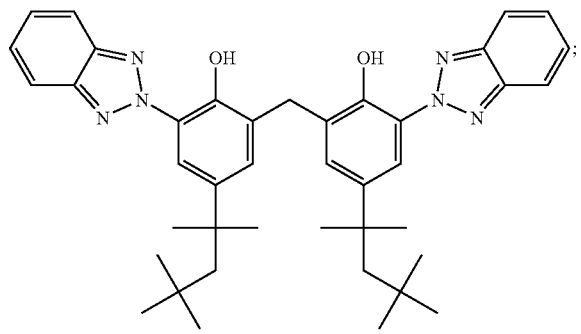

13. trianilino-s-triazine derivatives, for example 2,4,6-trianiline-(p-carbo-2′-ethyl-1′-oxy)-1,3,5-triazine and the UV absorbers disclosed in U.S. Pat. No. 5,332,568, EP-A-517 104, EP-A-507 691, WO 93/17002 and EP-A-570 838;
14. 2-phenylbenzimidazole-5-sulfonic acid and salts thereof;
15. menthyl o-aminobenzoate;
16. $TiO_2$ (variously encapsulated), ZnO and mica.

The UV absorbers described in "Sunscreens", Eds. N. J. Lowe, N. A. Shaath, Marcel Dekker, Inc., New York and Basle or in Cosmetics & Toiletries (107), 50ff (1992) also can be used as additional UV protective substances.

Special preference is given to the light-protective agents indicated in the following Table:

| INCI | Chemical Name | CAS No. |
|---|---|---|
| 3-BENZYLIDENE CAMPHOR | 1,7,7-trimethyl-3-(phenylmethylene)-bicyclo[2.2.1]heptan-2-one | 15087-24-8 |
| 4-METHYLBENZYLIDENE CAMPHOR | (+/−)-1,7,7-trimethyl-3-[(4-methylphenyl)-methylene]bicyclo[2.2.1]heptan-2-one | 36861-47-9 |
| BENZOPHENONE-10 | (2-hydroxy-4-methoxyphenyl)-(4-methylphenyl) methanone | 1641-17-4 |
| BENZOPHENONE-1 | 2,4-dihydroxybenzophenone | 131-56-6 |
| BENZOPHENONE-2 | 2,2′,4,4′-tetrahydroxybenzophenone | 131-55-5 |
| BENZOPHENONE-3 | 2-hydroxy-4-methoxybenzophenone; | 131-57-7 |
| BENZOPHENONE-4 | 2-hydroxy-4-methoxybenzophenone-5-sulfonic acid | 4065-45-6 |
| BENZOPHENONE-6 | 2,2′-dihydroxy-4,4′-dimethoxybenzophenone | 131-54-4 |
| BENZOPHENONE-8 | 2,2′-dihydroxy-4-methoxybenzophenone | 131-53-3 |
| BENZYLIDENE CAMPHOR SULFONIC ACID | alpha-(2-oxoborn-3-ylidene)-toluene-4-sulfonic acid and its salts | 56039-58-8 |
| BUTYL METHOXY-DIBENZOYLMETHANE | 1-[4-(1,1-dimethylethyl)phenyl]-3-(4-methoxyphenyl)propane-1,3-dione | 70356-09-1 |
| CAMPHOR BENZALKONIUM METHOSULFATE | methyl N,N,N-trimethyl-4-[(4,7,7-trimethyl-3-oxobicyclo[2,2,1]hept-2-ylidene)-methyl]anilinium sulfate | 52793-97-2 |
| CINOXATE | 2-ethoxyethyl p-methoxycinnamate | 104-28-9 |
| DEA-METHOXYCINNAMATE | diethanolamine salt of p-methoxy-hydrocinnamate | 56265-46-4 |
| DIISOPROPYL METHYL CINNAMATE | 2-propenoic acid, 3-[2,4-bis(1-methylethyl)phenyl]-, methyl ester | 32580-71-5 |
| DIPROPYLENE GLYCOL SALICYLATE | dipropylene glycol salicylate | 7491-14-7 |
| ETHYL DIHYDROXYPROPYL PABA | ethyl 4-bis(2-hydroxypropyl)-amino-benzoate | 58882-17-0 |
| ETHYL DIISOPROPYLCINNAMATE | ethyl 3-[2,4-bis(1-methylethyl)phenyl]-acrylate | 32580-72-6 |
| ETHYL METHOXYCINNAMATE | ethyl p-methoxycinnamate | 1929-30-2 |
| GLYCERYL OCTANOATE DIMETHOXYCINNAMATE | | |
| GLYCERYL PABA | glyceryl 1-(4-aminobenzoate) | 136-44-7 |
| HOMOSALATE | 3,3,5-trimethylcyclohexyl-2-hydroxy-benzoate | 118-56-9 |
| ISOAMYL p-METHOXYCINNAMATE | isopentyl p-methoxycinnamate | 71617-10-2 |
| ISOPROPYL DIBENZOYLMETHANE | 1-[4-(1-methylethyl)phenyl]-3-phenyl-propane-1,3-dione | 63250-25-9 |
| ISOPROPYL METHOXYCINNAMATE | isopropyl p-methoxycinnamate | 5466-76-2 |
| LAWSONE | 2-hydroxy-1,4-naphthoquinone | 83-72-7 |
| MENTHYL ANTHRANILATE | menthyl o-aminobenzoate | 134-09-8 |
| MENTHYL SALICYLATE | menthyl salicylate | 89-46-3 |
| OCTOCRYLENE | 2-ethylhexyl 2-cyano-3,3-diphenyl acrylate | 6197-30-4 |
| ETHYLHEXYL DIMETHYL PABA | 2-ethylhexyl 4-(dimethylamino)benzoate | 21245-02-3 |
| ETHYLHEXYL METHOXYCINNAMATE | 2-ethylhexyl 4-methoxycinnamate | 5466-77-3 |
| ETHYLHEXYL SALICYLATE | 2-ethylhexyl salicylate | 118-60-5 |
| ETHYLHEXYL TRIAZONE | benzoic acid, 4,4′,4″-(1,3,5-triazine-2,4,6-triyltriimino)tris-, tris(2-ethylhexyl) ester; 2,4,6-trianilino-(p-carbo-2′-ethylhexyl-1′-oxy)-1,3,5-triazine | 88122-99-0 |
| PABA | 4-aminobenzoic acid | 150-13-0 |
| PEG-25 PABA | benzoic acid, 4-amino-, ethyl ester, | 113010-52-9 |

-continued

| INCI | Chemical Name | CAS No. |
|---|---|---|
| | polymer with oxirane | |
| PENTYL DIMETHYL PABA | amyl dimethyl PABA | 14779-78-3 |
| PHENYLBENZIMIDAZOLE SULFONIC ACID | 2-phenyl-1H-benzimidazole-5-sulfonic acid | 27503-81-7 |
| POLYACRYLAMIDOMETHYL BENZYLIDENE CAMPHOR | | 113783-61-2 |
| TEA-SALICYLATE | triethanolamine salicylate | 2174-16-5 |
| TEREPHTHALYLIDENE DICAMPHOR SULFONIC ACID | 3,3'-(1,4-phenylenedimethylene)bis[7,7-dimethyl-2-oxo-bicyclo[2.2.1]heptane-1-methanesulfonic acid] | 90457-82-2 |
| TITANIUM DIOXIDE | titanium dioxide | 13463-67-7 |
| DIGALLOYL TRIOLEATE | digalloyl trioleate | 17048-39-4 |
| ZINC OXIDE | zinc oxide | 1314-13-2 |
| Methylene bis-benzotriazolyl tetramethylbutylphenol | 2,2'-methylene-bis[6-(2H-benzotriazol-2-yl)-4-(1,1,3,3-tetramethylbutyl)-phenol] | 103597-45-1 |
| Bis-ethylhexyloxyphenol methoxyphenyltriazine | 2,4-bis{[4-(2-ethylhexyloxy)-2-hydroxy]-phenyl}-6-(4-methoxyphenyl)-(1,3,5)-triazine | 187393-00-6 |
| BISIMIDAZYLATE | 1H-benzimidazole-4,6-disulfonic acid, 2,2'-(1,4-phenylene)bis-, disodium salt | 180898-37-7 |
| DIETHYLHEXYL BUTAMIDO TRIAZONE | benzoic acid, 4,4'-[[6-[[4-[[(1,1-dimethyl-ethyl)amino]carbonyl]phenyl]amino]-1,3,5-triazine-2,4-diyl]diimino]bis-, bis(2-ethyl-hexyl) ester | 154702-15-5 |
| DROMETRIZOLE TRISILOXANE | phenol, 2-(2H-benzotriazol-2-yl)-4-methyl-6-[2-methyl-3-[1,3,3,3-tetramethyl-1-[(trimethylsilyl)oxy]disiloxanyl]propyl]- | 155633-54-8 |
| BENZYLIDENE MALONATE POLYSILOXANE | alpha-(trimethylsilyl)-omega-(trimethyl-silyloxy) poly[oxy(dimethyl)silylene]-co-[oxy-(methyl)(2-{p-[2,2-bis(ethoxycarbonyl)vinyl]-phenoxy}-1-methyleneethyl)silylene]-co-[oxy-(methyl)(2-{p-[2,2-bis(ethoxycarbonyl)vinyl]-phenoxy}prop-1-enyl)silylene] | 207574-74-1 |
| | 2-(4-diethylamino-2-hydroxybenzoyl)-benzoic hexyl ester | 302776-68-7 |

Each of the above-mentioned light-protective agents, especially the light-protective agents in Table 1 indicated as being preferred, can be used in admixture with the UV absorbers according to the invention. It will be understood in that connection that, in addition to the UV absorbers according to the invention, it is also possible for more than one of the additional light-protective agents to be used, for example, two, three, four, five or six further light-protective agents.

Preference is given to the use of mixing ratios of UV absorbers according to the invention/further light-protective agents of from 1:99 to 99:1, especially from 1:95 to 95:1 and preferably from 10:90 to 90:10, based on weight. Of special interest are mixing ratios of from 20:80 to 80:20, especially from 40:60 to 60:40 and preferably of approximately 50:50. Such mixtures can be used, inter alia, to improve solubility or increase UV absorption.

Appropriate mixtures can be used especially advantageously in the cosmetic preparations described below.

The cosmetic preparations are suitable especially as UV filters, that is to say for the protection of organic materials that are sensitive to ultraviolet light, especially skin and hair, against the damaging effect of UV radiation.

The UV absorbers can be used either in the dissolved state or in the micronised state.

Any known process suitable for the preparation of microparticles can be used for the preparation of the micronised UV absorbers, for example:
  wet-grinding with a hard grinding medium, for example zirconium silicate and a protective surfactant or a protective polymer in water or in a suitable organic solvent;
  spray-drying from a suitable solvent, for example aqueous suspensions or suspensions containing organic solvents, or true solutions in water, ethanol, dichloroethane, toluene, N-methylpyrrolidone inter alia;
  by the expansion according to the RESS process (Rapid Expansion of Supercritical Solutions) of supercritical fluids (e.g. $CO_2$) in which the UV filter or filters is/are dissolved or the expansion of fluid carbon dioxide together with a solution of one or more UV filters in a suitable organic solvent;
  by reprecipitation from suitable solvents, including supercritical fluids (GASR process=Gas Anti-Solvent Recrystallisation/PCA process=Precipitation with Compressed Antisolvents).

As grinding apparatus for the preparation of the micronised organic UV absorbers there may be used, for example, a jet mill, ball mill, vibratory mill or hammer mill, preferably a high-speed mixing mill. The grinding is preferably carried out with a grinding aid, for example an alkylated vinylpyrrolidone polymer, a vinylpyrrolidone/vinyl acetate copolymer, an acyl glutamate, an alkyl polyglucoside, ceteareth-25 or a phospholipid.

The micronised UV absorbers so obtained usually have an average particle size that is from 0.02 to 2, preferably from 0.05 to 1.5, and more especially from 0.1 to 1.0, nm.

The UV absorbers can also be used dry in powder form. For that purpose the UV absorbers are subjected to known grinding methods, such as vacuum atomization, countercurrent spray-drying etc. Such powders have a particle size of from 0.1 nm to 2 μm. To avoid the occurrence of agglomeration, the UV absorbers can be coated with a surface-active compound prior to the pulverisation process, for example with an anionic, non-ionic or amphoteric surfactant, e.g. a phospholipid or a known polymer, such as PVP, an acrylate etc.

The cosmetic preparations contain, for example, from 0.1 to 30% by weight, preferably from 0.1 to 15% by weight and especially from 0.5 to 10% by weight, based on the total weight of the composition, of one or more UV absorbers and at least one cosmetically tolerable adjuvant.

The cosmetic preparations can be prepared by physically mixing the UV absorber(s) with the adjuvant using customary methods, for example by simply stirring together the individual components, especially by making use of the dissolution properties of already known cosmetic UV absorbers, for example OMC, salicylic acid isooctyl ester, inter alia. The UV absorber can be used, for example, without further treatment, or in the micronised state, or in the form of a powder.

The cosmetic preparations may be, for example, creams, gels, lotions, alcoholic and aqueous/alcoholic solutions, emulsions, wax/fat compositions, stick preparations, powders or ointments.

As water- and oil-containing emulsions (e.g. W/O, O/W, O/W/O and W/O/W emulsions or microemulsions) the preparations contain, for example, from 0.1 to 30% by weight, preferably from 0.1 to 15% by weight and especially from 0.5 to 10% by weight, based on the total weight of the composition, of one or more UV absorbers, from 1 to 60% by weight, especially from 5 to 50% by weight and preferably from 10 to 35% by weight, based on the total weight of the composition, of at least one oil component, from 0 to 30% by weight, especially from 1 to 30% by weight and preferably from 4 to 20 % by weight, based on the total weight of the composition, of at least one emulsifier, from 10 to 90% by weight, especially from 30 to 90% by weight, based on the total weight of the composition, of water, and from 0 to 88.9% by weight, especially from 1 to 50% by weight, of further cosmetically tolerable adjuvants.

As oil components of oil-containing compositions (e.g. oils, W/O, OW, O/W/O and W/O/W emulsions or microemulsions) there come into consideration, for example, Guerbet alcohols based on fatty alcohols having from 6 to 18, preferably from 8 to 10, carbon atoms, esters of linear $C_6$–$C_{24}$ fatty acids with linear $C_3$–$C_{24}$ alcohols, esters of branched $C_6$–$C_{13}$ carboxylic acids with linear $C_6$–$C_{24}$ fatty alcohols, esters of linear $C_6$–$C_{24}$ fatty acids with branched alcohols, especially 2-ethylhexanol, esters of hydroxycarboxylic acids with linear or branched $C_6$–$C_{22}$ fatty alcohols, especially dioctyl malates, esters of linear and/or branched fatty acids with polyhydric alcohols (for example propylene glycol, dimer diol or trimer triol) and/or Guerbet alcohols, triglycerides based on $C_6$–$C_{10}$ fatty acids, liquid mono-/di-/tri-glyceride mixtures based on $C_6$–$C_{18}$ fatty acids, esters of $C_6$–$C_{24}$ fatty alcohols and/or Guerbet alcohols with aromatic carboxylic acids, especially benzoic acid, esters of $C_2$–$C_{12}$ dicarboxylic acids with linear or branched alcohols having from 1 to 22 carbon atoms or polyols having from 2 to 10 carbon atoms and from 2 to 6 hydroxy groups, vegetable oils (such as sunflower oil, olive oil, soybean oil, rapeseed oil, almond oil, jojoba oil, orange oil, wheatgerm oil, peach kernel oil and the liquid components of coconut oil), branched primary alcohols, substituted cyclohexanes, linear and branched $C_6$–$C_{22}$ fatty alcohol carbonates, Guerbet carbonates, esters of benzoic acid with linear and/or branched $C_6$–$C_{22}$ alcohols (e.g. Finsolv® TN), linear or branched, symmetric or asymmetric dialkyl ethers having a total of from 12 to 36 carbon atoms, especially from 12 to 24 carbon atoms, for example di-n-octyl ether, di-n-decyl ether, di-n-nonyl ether, di-n-undecyl ether, di-n-dodecyl ether, n-hexyl n-octyl ether, n-octyl n-decyl ether, n-decyl n-undecyl ether, n-undecyl n-dodecyl ether, n-hexyl n-undecyl ether, di-tert-butyl ether, diisopentyl ether, di-3-ethyidecyl ether, tert-butyl n-octyl ether, isopentyl n-octyl ether and 2-methyl pentyl-n-octyl ether; ring-opening products of epoxidised fatty acid esters with polyols, silicone oils and/or aliphatic or naphthenic hydrocarbons. Also of importance are monoesters of fatty acids with alcohols having from 3 to 24 carbon atoms. That group of substances comprises the esterification products of fatty acids having from 8 to 24 carbon atoms, for example caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselinic acid, linoleic acid, linolenic acid, elaeostearic acid, arachidic acid, gadoleic acid, behenic acid and erucic acid and technical-grade mixtures thereof (obtained, for example, in the pressure removal of natural fats and oils, in the reduction of aldehydes from Roelen's oxosynthesis or in the dimerisation of unsaturated fatty acids) with alcohols, for example, isopropyl alcohol, caproic alcohol, capryl alcohol, 2-ethylhexyl alcohol, capric alcohol, lauryl alcohol, isotridecyl alcohol, myristyl alcohol, cetyl alcohol, palmoleyl alcohol, stearyl alcohol, isostearyl alcohol, oleyl alcohol, elaidyl alcohol, petroselinyl alcohol, linoyl alcohol, linolenyl alcohol, elaeostearyl alcohol, arachidyl alcohol, gadoleyl alcohol, behenyl alcohol, erucyl alcohol and brassidyl alcohol and technical-grade mixtures thereof (obtained, for example, in the high-pressure hydrogenation of technical-grade methyl esters based on fats and oils or aldehydes from Roelen's oxosynthesis and as monomer fractions in the dimerisation of unsaturated fatty alcohols). Of special importance are isopropyl myristate, isononanoic acid $C_{16}$–$C_{18}$ alkyl esters, stearic acid 2-ethylhexyl ester, cetyl oleate, glycerol tricaprylate, coconut fatty alcohol caprinate/caprylate and n-butyl stearate. Further oil components that can be used are dicarboxylic acid esters, such as di-n-butyl adipate, di(2-ethylhexyl) adipate, di(2-ethylhexyl) succinate and diisotridecyl acetate, and also diol esters, such as ethylene glycol dioleate, ethylene glycol diisotridecanoate, propylene glycol di(2-ethylhexanoate), propylene glycol diisostearate, propylene glycol dipelargonate, butanediol diisostearate and neopentyl glycol dicaprylate. Preferred mono- or poly-ols are ethanol, isopropanol, propylene glycol, hexylene glycol, glycerol and sorbitol. It is also possible to use di- and/or tri-valent metal salts (alkaline earth metal, $Al^{3+}$ inter alia) of one or more alkylcarboxylic acids.

The oil components can be used in an amount of, for example, from 1 to 60% by weight, especially from 5 to 50% by weight and preferably from 10 to 35% by weight, based on the total weight of the composition.

Any conventionally usable emulsifier can be used for the compositions.

As emulsifiers there come into consideration, for example, non-ionic surfactants from the following groups:
  addition products of from 2 to 30 mol of ethylene oxide and/or from 0 to 5 mol of propylene oxide with linear fatty alcohols having from 8 to 22 carbon atoms, with fatty acids having from 12 to 22 carbon atoms and with alkylphenols having from 8 to 15 carbon atoms in the alkyl group, for example ceteareth-20 or ceteareth-12;
  $C_{12}$–$C_{22}$ fatty acid mono- and di-esters of addition products of from 1 to 30 mol of ethylene oxide with polyols having from 3 to 6 carbon atoms, especially with glycerol;

glycerol mono- and di-esters and sorbitan mono- and di-esters of saturated and unsaturated fatty acids having from 6 to 22 carbon atoms and ethylene oxide addition products thereof, for example glyceryl stearates, glyceryl isostearates, glyceryl oleates, sorbitan oleates or sorbitan sesquioleates;

$C_8$–$C_{22}$alkyl-mono- and -oligo-glycosides and ethoxylated analogues thereof, degrees of oligomerisation of from 1.1 to 5, especially from 1.2 to 1.4, being preferred, and glucose being preferred as the sugar component;

addition products of from 2 to 60 mol. especially from 15 to 60 mol, of ethylene oxide with castor oil and/or hardened castor oil;

polyol esters and especially polyglycerol esters, for example diisostearoyl polyglyceryl-3-diisostearates, polyglyceryl-3-diisostearates, triglyceryl diisostearates, polyglyceryl-2-sesquiisostearates or polyglyceryl dimerates. Mixtures of compounds from a plurality of those substance classes are also suitable;

partial esters based on linear, branched, unsaturated or saturated $C_6$–$C_{22}$ fatty acids, ricinoleic acid and also 12-hydroxystearic acid and on glycerol, polyglycerol, pentaerythritol, dipentaerythritol, sugar alcohols (e.g. sorbitol), alkyl glucosides (e.g. methyl glucoside, butyl glucoside, lauryl glucoside) and also polyglucosides (e.g. cellulose), for example polyglyceryl-2-dihydroxystearates or polyglyceryl-2-diricinoleates;

mono-, di- and tri-alkylphosphates and also mono-, di- and/or tri-PEG-alkylphosphates and salts thereof;

wool wax alcohols;

one or more ethoxylated esters of natural derivatives, for example polyethoxylated esters of hydrogenated castor oil;

silicone oil emulsifiers, for example silicone polyol;

polysiloxane/polyalkyl/polyether copolymers and corresponding derivatives, for example cetyl dimethicone copolyol;

mixed esters of pentaerythritol, fatty acids, citric acid and fatty alcohol (see DE-A-1 165 574) and/or mixed esters of fatty acids having from 6 to 22 carbon atoms, methylglucose and polyols, preferably glycerol or polyglycerol, for example polyglyceryl-3-glucose distearates, polyglyceryl-3-glucose dioleates, methyl glucose dioleates or dicocoyl pentaerythryl distearyl citrates and also polyalkylene glycols.

The addition products of ethylene oxide and/or of propylene oxide with fatty alcohols, fatty acids, alkylphenols, glycerol mono- and di-esters and also sorbitan mono- and di-esters of fatty acids, or with castor oil, are known, commercially available products. They are usually homologue mixtures, the average degree of alkoxylation of which corresponds to the ratio of the amounts of ethylene oxide and/or propylene oxide and substrate with which the addition reaction is carried out. $C_{12}$–$C_{18}$ fatty acid mono- and di-esters of addition products of ethylene oxide with glycerol are known, for example, from DE-A-2 024 051 as fat-restoring substances for cosmetic preparations.

$C_1$–$C_{18}$Alkyl-mono- and -oligo-glycosides, their preparation and their use are known from the prior art. They are prepared especially by reacting glucose or oligosaccharides with primary alcohols having from 8 to 18 carbon atoms. Suitable glycoside radicals include mono-glycosides in which a cyclic sugar radical is glycosidically bonded to the fatty alcohol and also oligomeric glycosides having a degree of oligomerisation of up to preferably about 8. The degree of oligomerisation is a statistical average value based on a homologue distribution customary for such technical-grade products.

It is also possible to use zwitterionic surfactants as emulsifiers. The term "zwitterionic surfactants" denotes especially surface-active compounds that carry at least one quaternary ammonium group and at least one carboxylate and/or sulfonate group in the molecule. Zwitterionic surfactants that are especially suitable are the so-called betaines, such as N-alkyl-N,N-dimethylammonium glycinates, for example cocoalkyldimethylammonium glycinate, N-acylaminopropyl-N,N-dimethylammonium glycinates, for example cocoacylaminopropyldimethylammonium glycinate, and 2-alkyl-3-carboxymethyl-3-hydroxyethylimidazolines each having from 8 to 18 carbon atoms in the alkyl or acyl group and also cocoacylaminoethylhydroxyethylcarboxymethylglycinate. Special preference is given to the fatty acid amide derivative known by the CTFA name cocamidopropyl betaine. Likewise suitable as emulsifiers are ampholytic surfactants. Ampholytic surfactants are to be understood as meaning especially those which, in addition to containing a $C_8$–$C_{18}$-alkyl or -acyl group, contain at least one free amino group and at least one —COOH or —$SO_3$H group in the molecule and are capable of forming internal salts. Examples of suitable ampholytic surfactants include N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids, each having approximately from 8 to 18 carbon atoms in the alkyl group. Ampholytic surfactants to which special preference is given are N-cocoalkylaminopropionate, cocoacylaminoethylaminopropionate and $C_{12}$–$C_{18}$-acylsarcosine. In addition to the ampholytic emulsifiers there also come into consideration quaternary emulsifiers, special preference being given to those of the esterquat type, preferably methyl-quaternised di-fatty acid triethanolamine ester salts.

Non-ionic emulsifiers are preferred. Of the non-ionic emulsifiers mentioned, special preference is given to ethoxylated fatty alcohols having from 8 to 22 carbon atoms and from 4 to 30 EO units.

The emulsifiers may be used in an amount of, for example, from 1 to 30% by weight, especially from 4 to 20% by weight and preferably from 5 to 10% by weight, based on the total weight of the composition. It is, however, also possible in principle to dispense with the use of emulsifiers.

The preparations according to the invention, for example creams, gels, lotions, alcoholic and aqueous/alcoholic solutions, emulsions, wax/fat compositions, stick preparations, powders or ointments, may in addition contain, as further adjuvants and additives, mild surfactants, superfatting agents, pearlescent waxes, consistency regulators, thickeners, polymers, silicone compounds, fats, waxes, stabilisers, biogenic active ingredients, deodorising active ingredients, anti-dandruff agents, film formers, swelling agents, further UV light-protective factors, antioxidants, hydrotropic agents, preservatives, insect repellents, self-tanning agents, solubilisers, perfume oils, colourants, bacteria-inhibiting agents and the like.

Substances suitable for use as super-fatting agents are, for example, lanolin and lecithin and also polyethoxylated or acrylated lanolin and lecithin derivatives, polyol fatty acid esters, monoglycerides and fatty acid alkanolamides, the latter simultaneously acting as foam stabilisers.

Examples of suitable mild surfactants, that is to say surfactants especially well tolerated by the skin, include fatty alcohol polyglycol ether sulfates, monoglyceride sulfates, mono- and/or di-alkyl sulfosuccinates, fatty acid isethionates, fatty acid sarcosinates, fatty acid taurides, fatty acid glutamates, α-olefin sulfonates, ether carboxylic acids, alkyl oligoglucosides, fatty acid glucamides, alkylamidobetaines and/or protein fatty acid condensation products, the latter preferably being based on wheat proteins.

As pearlescent waxes there come into consideration, for example: alkylene glycol esters, especially ethylene glycol distearate; fatty acid alkanolamides, especially coco fatty acid di-ethanolamide; partial glycerides, especially stearic acid monoglyceride; esters of polyvalent, unsubstituted or hydroxy-substituted carboxylic acids with fatty alcohols having from 6 to 22 carbon atoms, especially long-chained esters of tartaric acid; fatty substances, for example fatty alcohols, fatty ketones, fatty aldehydes, fatty ethers and fatty carbonates, which in total have at least 24 carbon atoms, especially laurone and distearyl ether; fatty acids, such as stearic acid, hydroxystearic acid or behenic acid, ring-opening products of olefin epoxides having from 12 to 22 carbon atoms with fatty alcohols having from 12 to 22 carbon atoms and/or polyols having from 2 to 15 carbon atoms and from 2 to 10 hydroxy groups, and mixtures thereof.

As consistency regulators there come into consideration especially fatty alcohols or hydroxy fatty alcohols having from 12 to 22 carbon atoms and preferably from 16 to 18 carbon atoms, and in addition partial glycerides, fatty acids and hydroxy fatty acids. Preference is given to a combination of such substances with alkyl-oligoglucosides and/or fatty acid N-methylglucamides of identical chain length and/or polyglycerol poly-12-hydroxystearates. Suitable thickeners include, for example, Aerosil types (hydrophilic silicic acids), polysaccharides, especially xanthan gum, guar-guar, agar-agar, alginates and Tyloses, carboxymethyl cellulose and hydroxymethyl cellulose, also relatively high molecular weight polyethylene glycol mono- and di-esters of fatty acids, polyacrylates (e.g. Carbopol® from Goodrich or Synthalen® from Sigma), polyacrylamides, polyvinyl alcohol and polyvinylpyrrolidone, surfactants, for example ethoxylated fatty acid glycerides, esters of fatty acids with polyols, for example pentaerythritol or trimethylolpropane, fatty alcohol ethoxylates with restricted homologue distribution and alkyl-oligoglucosides as well as electrolytes, such as sodium chloride or ammonium chloride.

Suitable cationic polymers are, for example, cationic cellulose derivatives, for example a quaternised hydroxymethyl cellulose obtainable under the name Polymer JR 400® from Amerchol, cationic starch, copolymers of diallylammonium salts and acrylamides, quaternised vinylpyrrolidone/vinyl imidazole polymers, for example Luviquate® (BASF), condensation products of polyglycols and amines, quaternised collagen polypeptides, for example lauryldimonium hydroxypropyl hydrolyzed collagen (Lamequat®L/Grünau), quaternised wheat polypeptides, polyethyleneimine, cationic silicone polymers, for example amidomethicones, copolymers of adipic acid and dimethylaminohydroxypropyldiethylenetriamine (Cartaretin®/Sandoz), copolymers of acrylic acid with dimethyidiallylammonium chloride (Merquate® 550/Chemviron), polyaminopolyamides, as described, for example, in FR-A-2 252 840, and the crosslinked water-soluble polymers thereof, cationic chitin derivatives, for example of quaternised chitosan, optionally distributed as microcrystals; condensation products of dihaloalkyls, for example dibromobutane, with bisdialkylamines, for example bisdimethylamino-1,3-propane, cationic guar gum, for example Jaguar® C-17, Jaguar® C-16 from Celanese, quaternised ammonium salt polymers, for example Mirapol® A-15, Mirapolo® AD-1, Mirapol® AZ-1 from Miranol.

As anionic, zwitterionic, amphoteric and non-ionic polymers there come into consideration, for example, vinyl acetate/crotonic acid copolymers, vinylpyrrolidone/vinyl acrylate copolymers, vinyl acetate/butyl maleate/isobornyl acrylate copolymers, methyl vinyl ether/maleic anhydride copolymers and esters thereof, uncrosslinked polyacrylic acids and polyacrylic acids crosslinked with polyols, acrylamidopropyltrimethylammonium chloride/acrylate copolymers, octyl acrylamide/methyl methacrylate/tert-butylaminoethyl methacrylate/2-hydroxypropyl methacrylate copolymers, polyvinylpyrrolidone, vinylpyrrolidone/vinyl acetate copolymers, vinylpyrrolidone/dimethylaminoethyl methacrylate/vinyl caprolactam terpolymers and also optionally derivatised cellulose ethers and silicones.

Suitable silicone compounds are, for example, dimethylpolysiloxanes, methylphenylpolysiloxanes, cyclic silicones, and also amino-, fatty acid-, alcohol-, polyether-, epoxy-, fluorine-, glycoside- and/or alkyl-modified silicone compounds, which at room temperature may be in either liquid or resinous form. Also suitable are simethicones, which are mixtures of dimethicones having an average chain length of from 200 to 300 dimethylsiloxane units with hydrogenated silicates. A detailed survey by Todd et al. of suitable volatile silicones may in addition be found in Cosm. Toil. 91, 27 (1976).

Typical examples of fats are glycerides, and as waxes there come into consideration, inter alia, beeswax, carnauba wax, candelilla wax, montan wax, paraffin wax, hydrogenated castor oils and fatty acid esters or microwaxes solid at room temperature optionally in combination with hydrophilic waxes, e.g. cetylstearyl alcohol or partial glycerides. Metal salts of fatty acids, for example magnesium, aluminium and/or zinc stearate or ricinoleate, may be used as stabilisers.

Biogenic active ingredients are to be understood as meaning, for example, tocopherol, tocopherol acetate, tocopherol palmitate, ascorbic acid, deoxyribonucleic acid, retinol, bisabolol, allantoin, phytantriol, panthenol, AHA acids, amino acids, ceramides, pseudoceramides, essential oils, plant extracts and vitamin complexes.

As deodorising active ingredients there come into consideration, for example, antiperspirants, for example aluminium chlorohydrates (see J. Soc. Cosm. Chem. 24, 281 (1973)). Under the trade mark Locron® of Hoechst AG, Frankfurt (FRG), there is available commercially, for example, an aluminium chlorohydrate corresponding to formula $Al_2(OH)_5Cl \times 2.5\ H_2O$, the use of which is especially preferred (see J. Pharm. Pharmacol. 26, 531 (1975)). Besides the chlorohydrates, it is also possible to use aluminium hydroxy-acetates and acidic aluminium/zirconium salts. Esterase inhibitors may be added as further deodorising active ingredients. Such inhibitors are preferably trialkyl citrates, such as trimethyl citrate, tripropyl citrate, triisopropyl citrate, tributyl citrate and especially triethyl citrate (Hydagen® CAT, Henkel KGaA, Dusseldorf/FRG), which inhibit enzyme activity and hence reduce odour formation. Further substances that come into consideration as esterase inhibitors are sterol sulfates or phosphates, for example lanosterol, cholesterol, campesterol, stigmasterol and sitosterol sulfate or phosphate, dicarboxylic acids and esters thereof, for example glutaric acid, glutaric acid monoethyl ester, glutaric acid diethyl ester, adipic acid, adipic acid monoethyl ester, adipic acid diethyl ester, malonic acid and malonic acid diethyl ester and hydroxycarboxylic acids and esters thereof, for example citric acid, malic acid, tartaric acid or tartaric acid diethyl ester. Antibacterial active ingredients that influence the microbial flora and kill or inhibit the growth of sweat-decomposing bacteria can likewise be present in the preparations (especially in stick preparations). Examples include chitosan, phenoxyethanol and chlorhexidine gluconate. 5–Chloro-2-(2,4-dichlorophenoxy)-phenol (Irgasan®, Ciba Specialty Chemicals Inc.) has also proved especially effective.

As anti-dandruff agents there may be used, for example, climbazole, octopirox and zinc pyrithione. Customary film formers include, for example, chitosan, microcrystalline chitosan, quaternised chitosan, polyvinylpyrrolidone, vinylpyrrolidone/vinyl acetate copolymers, polymers of quaternary cellulose derivatives containing a high proportion of acrylic acid, collagen, hyaluronic acid and salts thereof and similar compounds. As swelling agents for aqueous phases there may be used montmorillonites, clay mineral substances, Pemulen and also alkyl-modified types of Carbopol (Goodrich). Further suitable polymers and swelling agents can be found in the review by R. Lochhead in Cosm. Toil. 108, 95 (1993).

In addition to the primary light-protective substances it is also possible to use secondary light-protective substances of the antioxidant kind which interrupt the photochemical reaction chain triggered when UV radiation penetrates the skin or hair. Typical examples of such antioxidants are amino acids (e.g. glycine, histidine, tyrosine, tryptophan) and derivatives thereof, imidazoles (e.g. urocanic acid) and derivatives thereof, peptides, such as D,L-carnosine, D-carnosine, L-carnosine and derivatives thereof (e.g. anserine), carotinoids, carotenes (e.g. α-carotene, β-carotene, lycopene) and derivatives thereof, chlorogenic acid and derivatives thereof, lipoic acid and derivatives thereof (e.g. dihydrolipoic acid), aurothioglycose, propylthiouracil and other thiols (e.g. thioredoxin, glutathione, cysteine, cystine, cystamine and the glycosyl, N-acetyl, methyl, ethyl, propyl, amyl, butyl, lauryl, palmitoyl, oleyl, γ-linoleyl, cholesteryl and glyceryl esters thereof) and also salts thereof, dilauryl thiodipropionate, distearyl thiodipropionate, thiodipropionic acid and derivatives thereof (esters, ethers, peptides, lipids, nucleotides, nucleosides and salts) and also sulfoximine compounds (e.g. buthionine sulfoximines, homocysteine sulfoximine, buthionine sulfones, penta-, hexa-, hepta-thionine sulfoximine) in very small tolerable amounts (e.g. from pmol to μmol/kg), also (metal) chelating agents (e.g. α-hydroxy fatty acids, palmitic acid phytic acid, lactoferrin), α-hydroxy acids (e.g. citric acid, lactic acid, malic acid), humic acid, bile acid, bile extracts, bilirubin, biliverdin, EDTA, ECTA and derivatives thereof, unsaturated fatty acids and derivatives thereof (e.g. γ-linolenic acid, linoleic acid, oleic acid), folic acid and derivatives thereof, ubiquinone and ubiquinol and derivatives thereof, vitamin C and derivatives (e.g. ascorbyl palmitate, magnesium ascorbyl phosphate, ascorbyl acetate), tocopherols and derivatives (e.g. vitamin E acetate), vitamin A and derivatives (e.g. vitamin A palmitate) and also coniferyl benzoate of benzoin resin, rutinic acid and derivatives thereof, α-glycosylrutin, ferulic acid, furfurylidene glucitol, carnosine, butyl hydroxytoluene, butyl hydroxyanisole, resinous nordihydroguaiaretic acid, nordihydroguaiaretic acid, trihydroxybutyrophenone, uric acid and derivatives thereof, mannose and derivatives thereof, superoxide dismutase, N-[3-(3,5-di-tert-butyl-4-hydroxyphenyl)propionyl] sulfanilic acid (and salts thereof, for example the disodium salts), zinc and derivatives thereof (e.g. ZnO, $ZnSO_4$), selenium and derivatives thereof (e.g. selenium methionine), stilbene and derivatives thereof (e.g. stilbene oxide, trans-stilbene oxide) and the derivatives suitable according to the invention (salts, esters, ethers, sugars, nucleotides, nucleosides, peptides and lipids) of those mentioned active ingredients. HALS (="Hindered Amine Light Stabilizers") compounds may also be mentioned. The amount of antioxidants present is usually from 0.001 to 30% by weight, preferably from 0.01 to 3% by weight, based on the weight of the UV absorber(s).

To improve the flow behaviour it is also possible to employ hydrotropic agents, for example ethanol, isopropyl alcohol or polyols. The polyols that come into consideration for that purpose have preferably from 2 to 15 carbon atoms and at least two hydroxy groups.

The polyols may also contain further functional groups, especially amino groups, and/or may be modified with nitrogen. Typical examples are as follows:

glycerol;

alkylene glycols, for example ethylene glycol, diethylene glycol, propylene glycol, butylene glycol, hexylene glycol and also polyethylene glycols having an average molecular weight of from 100 to 1000 dalton;

technical oligoglycerol mixtures having an intrinsic degree of condensation of from 1.5 to 10, for example technical diglycerol mixtures having a diglycerol content of from 40 to 50% by weight;

methylol compounds, such as, especially, trimethylolethane, trimethylolpropane, trimethylolbutane, pentaerythritol and dipentaerythritol;

lower alkyl-glucosides, especially those having from 1 to 8 carbon atoms in the alkyl radical, for example methyl and butyl glucoside;

sugar alcohols having from 5 to 12 carbon atoms, for example sorbitol or mannitol;

sugars having from 5 to 12 carbon atoms, for example glucose or saccharose;

amino sugars, for example glucamine;

dialcohol amines, such as diethanolamine or 2-amino-1, 3-propanediol.

Suitable preservatives include, for example, phenoxyethanol, formaldehyde solution, Parabens, pentanediol or sorbic acid and the further substance classes listed in Schedule 6, Parts A and B of the Cosmetics Regulations.

There may be mentioned as perfume oils mixtures of natural and/or synthetic aromatic substances. Natural aromatic substances are, for example, extracts from blossom (lilies, lavender, roses, jasmine, neroli, ylang-ylang), from stems and leaves (geranium, patchouli, petitgrain), from fruit (aniseed, coriander, carraway, juniper), from fruit peel (bergamot, lemons, oranges), from roots (mace, angelica, celery, cardamom, costus, iris, calmus), from wood (pinewood, sandalwood, guaiacum wood, cedarwood, rosewood), from herbs and grasses (tarragon, lemon grass, sage, thyme), from needles and twigs (spruce, pine, Scots pine, mountain pine), from resins and balsams (galbanum, elemi, benzoin, myrrh, olibanum, opoponax). Animal raw materials also come into consideration, for example civet and castoreum. Typical synthetic aromatic substances are, for example, products of the ester, ether, aldehyde, ketone, alcohol or hydrocarbon type.

Aromatic substance compounds of the ester type are, for example, benzyl acetate, phenoxyethyl isobutyrate, p-tert-butylcyclohexyl acetate, linalyl acetate, dimethylbenzyl-carbinyl acetate, phenylethyl acetate, linalyl benzoate, benzyl formate, ethylmethylphenyl glycinate, allylcyclohexyl propionate, styrallyl propionate and benzyl salicylate. The ethers include, for example, benzyl ethyl ether; the aldehydes include, for example, the linear alkanals having from 8 to 18 hydrocarbon atoms, citral, citronellal, citronellyl oxyacetaldehyde, cyclamen aldehyde, hydroxycitronellal, lilial and bourgeonal; the ketones include, for example, the ionones, α-isomethylionone and methyl cedryl ketone; the alcohols include, for example, anethol, citronellol, eugenol, isoeugenol, geraniol, linalool, phenyl ethyl alcohol and terpinol; and the hydrocarbons include mainly the terpenes and balsams. It is preferable, however, to use mixtures of various aromatic substances that together produce an attractive scent. Ethereal oils of relatively low volatility, which are chiefly used as aroma components, are also suitable as perfume oils, e.g. sage oil, camomile oil, clove oil, melissa oil, oil of cinnamon leaves, lime blossom oil, juniper berry oil, vetiver oil, olibanum oil, galbanum oil, labolanum oil and lavandin oil. Preference is given to the use of bergamot oil, dihydromyrcenol, lilial, lyral, citronellol, phenyl ethyl alcohol, α-hexyl cinnamaldehyde, geraniol, benzyl acetone, cyclamen aldehyde, linalool, boisambrene forte, ambroxan, indole, hedione, sandelice, lemon oil, tangerine oil, orange oil, allyl amyl glycolate, cyclovertal, lavandin oil, muscatel sage oil, β-damascone, bourbon geranium oil, cyclohexyl salicylate, vertofix coeur, iso-E-Super, Fixolide NP, evernyl, iraldein gamma, phenylacetic acid, geranyl acetate, benzyl acetate, rose oxide, romillat, irotyl and floramat alone or in admixture with one another.

There may be used as colourants the substances that are suitable and permitted for cosmetic purposes, as compiled, for example, in the publication "Kosmetische Färbemittel" of the Farbstoffkommission der Deutschen Forschungsgemeinschaft, Verlag Chemie, Weinheim, 1984, pages 81 to 106. The colourants are usually used in concentrations of from 0.001 to 0.1% by weight, based on the total mixture.

Typical examples of bacteria-inhibiting agents are preservatives that have a specific action against gram-positive bacteria, such as 2,4,4'-trichloro-2'-hydroxydiphenyl ether, chlorhexidine (1,6-di(4-chlorophenyl-biguanido)hexane) or TCC (3,4,4'-trichlorocarbanilide). A large number of aromatic substances and ethereal oils also have antimicrobial properties.

Typical examples are the active ingredients eugenol, menthol and thymol in clove oil, mint oil and thyme oil. A natural deodorising agent of interest is the terpene alcohol farnesol (3,7,11-trimethyl-2,6,10-dodecatrien-1-ol), which is present in lime blossom oil. Glycerol monolaurate has also proved to be a bacteriostatic agent. The amount of the additional bacteria-inhibiting agents present is usually from 0.1 to 2% by weight, based on the solids content of the preparations.

It is furthermore possible for the cosmetic preparations to contain, as adjuvants, anti-foams, such as silicones, structurants, such as maleic acid, solubilisers, such as ethylene glycol, propylene glycol, glycerol or diethylene glycol, opacifiers, such as latex, styrene/PVP or styrene/acrylamide copolymers, complexing agents, such as EDTA, NTA, β-alaninediacetic acid or phosphonic acids, propellants, such as propane/butane mixtures, $N_2O$, dimethyl ether, $CO_2$, $N_2$ or air, so-called coupler and developer components as oxidation dye precursors, reducing agents, such as thioglycolic acid and derivatives thereof, thiolactic acid, cysteamine, thiomalic acid or α-mercaptoethanesulfonic acid, or oxidising agents, such as hydrogen peroxide, potassium bromate or sodium bromate.

There come into consideration as insect repellents, for example, N,N-diethyl-m-toluamide, 1,2-pentanediol or insect repellent 3535; suitable self-tanning agents are, for example, dihydroxyacetone, erythrulose or mixtures of dihydroxyacetone and erythrulose.

Cosmetic formulations according to the invention are contained in a wide variety of cosmetic preparations. There come into consideration, for example, especially the following preparations:

- skin-care preparations, e.g. skin-washing and cleansing preparations in the form of tablet-form or liquid soaps, synthetic detergents or washing pastes,
- bath preparations, e.g. liquid (foam baths, milks, shower preparations) or solid bath preparations, e.g. bath cubes and bath salts;
- skin-care preparations, e.g. skin emulsions, multi-emulsions or skin oils;
- cosmetic personal care preparations, e.g. facial make-up in the form of day creams or powder creams, face powder (loose or pressed), rouge or cream make-up, eye-care preparations, e.g. eyeshadow preparations, mascara, eyeliner, eye creams or eye-fix creams; lip-care preparations, e.g. lipsticks, lip gloss, lip contour pencils, nail-care preparations, such as nail varnish, nail varnish removers, nail hardeners or cuticle removers;
- foot-care preparations, e.g. foot baths, foot powders, foot creams or foot balsams, special deodorants and anti-perspirants or callus-removing preparations;
- light-protective preparations, such as sun milks, lotions, creams or oils, sunblocks or tropicals, pre-tanning preparations or after-sun preparations;
- skin-tanning preparations, e.g. self-tanning creams;
- depigmenting preparations, e.g. preparations for bleaching the skin or skin-lightening preparations;
- insect-repellents, e.g. insect-repellent oils, lotions, sprays or sticks;
- deodorants, such as deodorant sprays, pump-action sprays, deodorant gels, sticks or roll-ons;
- antiperspirants, e.g. antiperspirant sticks, creams or roll-ons;
- preparations for cleansing and caring for blemished skin, e.g. synthetic detergents (solid or liquid), peeling or scrub preparations or peeling masks;
- hair-removal preparations in chemical form (depilation), e.g. hair-removing powders, liquid hair-removing preparations, cream- or paste-form hair-removing preparations, hair-removing preparations in gel form or aerosol foams;
- shaving preparations, e.g. shaving soap, foaming shaving creams, non-foaming shaving creams, foams and gels, preshave preparations for dry shaving, aftershaves or aftershave lotions;
- fragrance preparations, e.g. fragrances (eau de Cologne, eau de toilette, eau de parfum, parfum de toilette, perfume), perfume oils or perfume creams;
- cosmetic hair-treatment preparations, e.g. hair-washing preparations in the form of shampoos and conditioners, hair-care preparations, e.g. pretreatment preparations, hair tonics, styling creams, styling gels, pomades, hair rinses, treatment packs, intensive hair treatments, hair-structuring preparations, e.g. hair-waving preparations for permanent waves (hot wave, mild wave, cold wave), hair-straightening preparations, liquid hair-setting preparations, hair foams, hairsprays, bleaching preparations, e.g. hydrogen peroxide solutions, lightening shampoos, bleaching creams, bleaching powders, bleaching pastes or oils, temporary, semi-permanent or permanent hair colourants, preparations containing self-oxidising dyes, or natural hair colourants, such as henna or camomile.

The final formulations listed may exist in a variety of presentation forms, for example:
in the form of liquid preparations as a W/O, O/W, O/W/O, W/O/W or PIT emulsion and all kinds of microemulsions,
in the form of a gel,
in the form of an oil, a cream, milk or lotion,
in the form of a powder, a lacquer, a tablet or make-up,
in the form of a stick,
in the form of a spray (spray with propellant gas or pump-action spray) or an aerosol,
in the form of a foam, or
in the form of a paste.

Of special importance as cosmetic preparations for the skin are light-protective preparations, such as sun milks, lotions, creams, oils, sunblocks or tropicals, pretanning preparations or after-sun preparations, also skin-tanning preparations, for example self-tanning creams. Of particular interest are sun protection creams, sun protection lotions, sun protection oils, sun protection milk and sun protection preparations in the form of a spray.

Of special importance as cosmetic preparations for the hair are the above-mentioned preparations for hair treatment, especially hair-washing preparations in the form of shampoos, hair conditioners, hair-care preparations, e.g. pretreatment preparations, hair tonics, styling creams, styling gels, pomades, hair rinses, treatment packs, intensive hair treatments, hair-straightening preparations, liquid hair-setting preparations, hair foams and hairsprays. Of special interest are hair-washing preparations in the form of shampoos.

A shampoo has, for example, the following composition: from 0.01 to 5% by weight of a UV absorber according to the invention, 12.0% by weight of sodium laureth-2-sulfate, 4.0% by weight of cocamidopropyl betaine, 3.0% by weight of sodium chloride, and water ad 100%.

For example, especially the following hair-cosmetic formulations may be used:
a₁) spontaneously emulsifying stock formulation, consisting of the UV absorber according to the invention, PEG-6–C₁₀oxoalcohol and sorbitan sesquioleate, to which water and any desired quaternary ammonium compound, for example 4% minkamidopropyl dimethyl-2-hydroxyethylammonium chloride or Quaternium 80 is added;
a₂) spontaneously emulsifying stock formulation consisting of the UV absorber according to the invention, tributyl citrate and PEG-20-sorbitan monooleate, to which water and any desired quaternary ammonium compound, for example 4% minkamidopropyl dimethyl-2-hydroxyethylammonium chloride or Quaternium 80 is added;
b) Quat-doped solutions of the UV absorber according to the invention in butyl triglycol and tributyl citrate;
c) mixtures or solutions of the UV absorber according to the invention with n-alkylpyrrolidone.

The cosmetic preparation according to the invention is distinguished by excellent protection of human skin against the damaging effect of sunlight. In the following Examples, percentages relate to weight. The amounts of the triazine derivatives used relate to the pure substance.

PREPARATION EXAMPLES OF THE NOVEL COMPOUNDS

Example 1

A suspension of 7 g (0.05 mol) of dimedone and 14.8 g (0.1 mol) of orthoformic acid triethyl ester in 15 ml of isobutanol is maintained at reflux for 2 hours. After cooling to room temperature, 4.6 g (0.025 mol) of 2,4-diamino-6-phenyl-1,3,5-triazine and 3 drops of trifluoromethanesulfonic anhydride are added. The reaction mixture is maintained at reflux for 20 hours and then cooled to room temperature. The resulting crude product is filtered off. The colourless product is obtained by column chromatography (silica gel) using a 9:1 mixture of dichloromethane and methanol as eluant and is dried at 60° C. in vacuo.

Yield: 1 g (8% of theory).

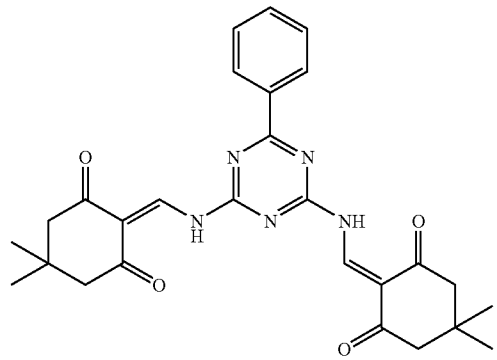

(101)

$\lambda_{max}$=320 nm; $\epsilon$=50 970, E (=extinction value) (1%, 1 cm)=1045.

$\gamma_{max}$=224 nm; $\epsilon$=35 699, E (1%, 1 cm)=732.

Example 2

0.1 ml of trifluoromethanesulfonic anhydride is added, at 90° C., to a solution of 7.5 g (0.05 mol) of orthoformic acid triethyl ester in 50 ml of isobutanol. 2.3 g (0.0125 mol) of 2,2-diamino-6-phenyl-1,3,5-triazine are then introduced in portions in the course of 1.5 hours. The resulting solution is stirred for 30 minutes at 100° C. After the addition of 2.3 g (0.025 mol) of acetylacetone, the reaction mixture is maintained at reflux for 4 hours. After cooling to room temperature, the suspension is filtered. The filter cake is recrystallised from ethyl acetate and dried in vacuo at 70° C. Yield: 1.3 g (26% of theory).

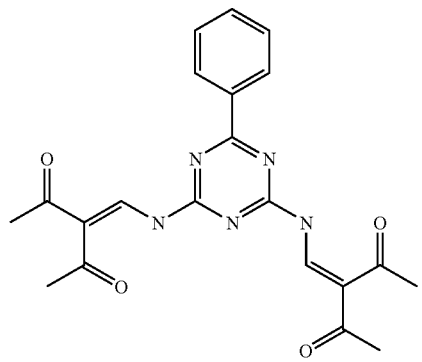

(102)

$\lambda_{max}$=322 nm; $\epsilon$=42 906, E (1%, 1 cm)=1053 (in ethanol).

Example 3

7.2 g (0.05 mol) of malonic acid cyclic isopropylidene ester, 14.8 g (0.1 mol) of orthoformic acid triethyl ester and 4.6 g (0.025 mol) of diaminophenyltriazine are mixed in 150 ml of toluene and then maintained at reflux for 1 hour. In the course of 2 hours, 2.5 g of phosphoryl chloride are added dropwise and the reaction mixture is refluxed for a further 2 hours. After cooling to room temperature, 100 ml of water and 100 ml of ethyl acetate are added. The organic phase is separated off and heated for 30 minutes at 40-50° C. together with 5 g of sodium sulfate and 5 g of Tonsil. After filtration of the mixture while it is still warm, the filtrate is concentrated to dryness by evaporation. Subsequent column chromatography (silica gel) using a 7:3 mixture of toluene and acetone yields the pure product, which is dried in vacuo at 80° C. Yield: 5 g (40% of theory).

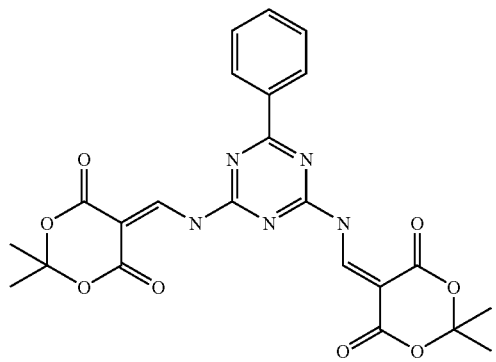

(103)

$\lambda_{max}$=332 nm; $\epsilon$=68 068, E (1%, 1 cm)=1374 (in dioxane).

Example 4

In a sulfonating flask equipped with a reflux condensor and a calcium chloride drying tube, 4.78 g (0.025 mol) of 2,4-diamino-6-phenyl-1,3,5-triazine, 9.96 g (0.075 mol) of ethyl aceto-acetate, 8.12 g (0.075 mol) of orthoformic acid trimethyl ester and 1.03 g (0.006 mol) of copper(II) chloride dihydrate are mixed in 50 ml of dimethylacetamide and stirred for 3 hours at 70° C. After cooling to room temperature, the reaction mixture is stirred into 200 ml of 10% sodium sulfate solution. The precipitate that forms is filtered off, washed neutral with water and recrystallised from ethanol. The product is dried in vacuo at 60° C.

Yield: 4.1 g (35% of theory).

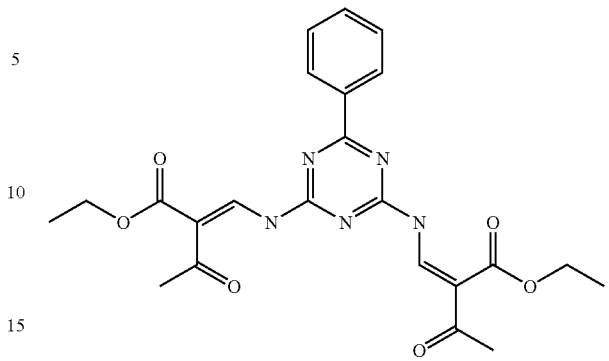

(104)

Yield: 4.1 g (35% of theory)

$\lambda_{max}$=319 nm; $\epsilon$=45 969, E (1%, 1 cm)=983 (in ethanol).

Example 5

3.22 g (0.025 mol) of melamine, 14.94 g (0.1125 mol) of ethyl acetoacetate, 12.18 g (0.1125 mol) of orthoformic acid trimethyl ester and 1.03 g (0.006 mol) of copper(II) chloride dihydrate are stirred in 50 ml of N-methylpyrrolidone for 4 hours at 80° C. The cold reaction mixture is added to 400 ml of 5% aqueous sodium sulfate solution. The resulting precipitate is filtered off, washed with water and recrystallised from ethanol. The product is dried in vacuo at 60° C. Yield: 6.5 g (48% of theory).

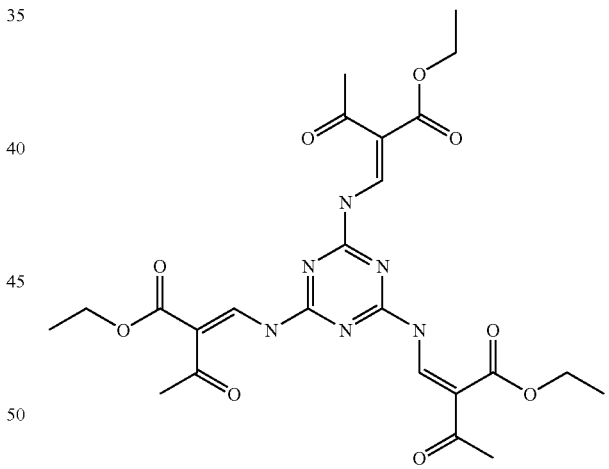

(105)

$\lambda_{max}$=325 nm; $\epsilon$=790448, E (1%, 1 cm)=1350 (in dioxane).

Example 6

3.22 g (0.025 mol) of melamine, 16.60 g (0.113 mol) of malonic acid cyclic isopropylidene ester, 17.09 g (0.113 mol) of orthoformic acid triethyl ester and 1.03 g (0.006 mol) of copper(II) chloride dihydrate are stirred in 50 ml of N-methylpyrrolidone for 6 hours at 80° C. The cold reaction mixture is added to 400 ml of 5% aqueous sodium sulfate solution. The resulting precipitate is filtered off, washed with water and copious amounts of ethanol. The product is dried in vacuo at 60° C. Yield: 6.2 g (42% of theory).

(106)

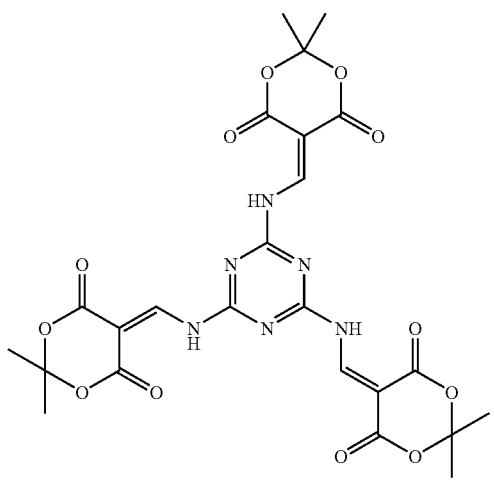

$\lambda_{max}$=326 nm; $\epsilon$=61 956, E (1%, 1 cm)=1053 (in dioxane).

Example 6

Parallel Syntheses of the Compounds of the General Formula

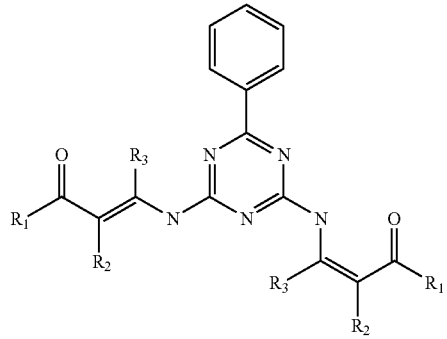

General Procedure:

2,4-Diamino-6-phenyl-1,3,5-triazine (0.0013 mol, 0.24 g) is dissolved in N-methylpyrrolidone (1.15 ml). Orthoformic acid trimethyl ester (0.0038 mol, 0.42 ml), copper chloride dihydrate solution (0.0013 mol. 0.22 g in 0.5 ml of NMP) and the appropriate ketone (0.0038 mol dissolved in 2 ml of NMP) are added to the solution. The reaction mixture is shaken for 4 hours at 70° C. The crude product is precipitated by the addition of 10 ml of 10% aqueous sodium sulfate solution, and the precipitate is then filtered off and washed with copious amounts of ethanol. Subsequent column chromatography (Nucleosil 5C18) using a mixture of acetonitrile and water yields the pure product.

Example 7

Parallel Syntheses of the Compounds of Formula

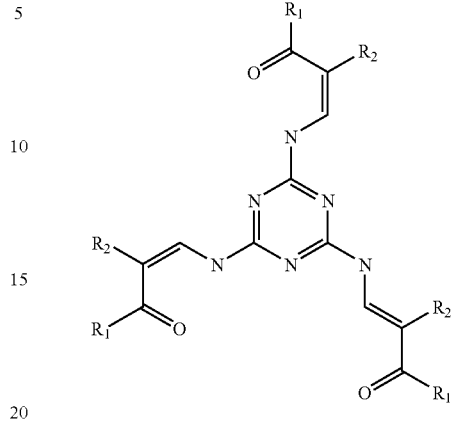

General Procedure:

Melamine (0.0013 mol, 0.17 g) is dissolved in N-methylpyrrolidone (1.42 ml). Orthoformic acid trimethyl ester (0.0057 mol, 0.59 ml), copper chloride dihydrate solution (0.0013 mol. 0.22 g in 0.5 ml of NMP) and the appropriate ketone (0.0057 mol dissolved in 2 ml of NMP) are added to the solution. The reaction mixture is shaken for 4 hours at 80° C. The crude product is precipitated by the addition of 10 ml of 10% aqueous sodium sulfate solution, and the precipitate is then filtered off and washed with copious amounts of ethanol. Subsequent column chromatography (Nucleosil 5C18)) using a mixture of acetonitrile and water yields the pure product.

Example 8

Parallel Syntheses of the Compounds of Formula

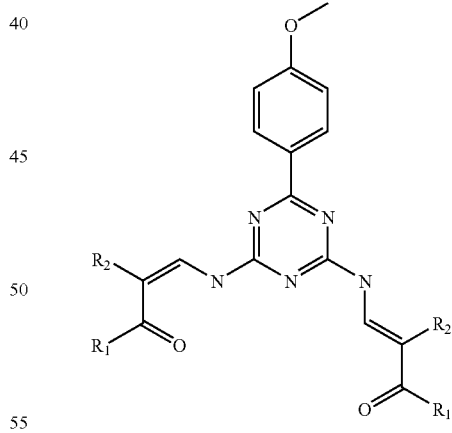

General Procedure:

2,4-Diamino-6-p-methoxyphenyl-1,3,5-triazine (0.0005 mol, 0.11 g) is dissolved in N-methylpyrrolidone (0.6 ml). Orthoformic acid trimethyl ester (0.0013 mol, 0.14 g), copper chloride dihydrate solution (0.0013 mol, 0.22 g in 0.5 ml of NMP) and the appropriate ketone (0.0005 mol dissolved in 0.23 ml of NMP) are added to the solution. The reaction mixture is shaken for 4 hours at 80° C. The crude product is precipitated by the addition of 10 ml of 10% aqueous sodium sulfate solution, and the precipitate is then filtered off and washed with copious amounts of ethanol.

Subsequent column chromatography (Nucleosil 5C18)) using a mixture of acetonitrile and water yields the pure product.

Example 9

Parallel Syntheses of the Compounds of Formula

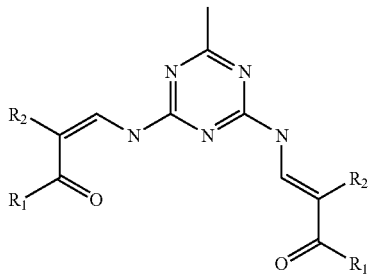

General Procedure:

2,4-Diamino-6-methyl-1,3,5-triazine (0.0013 mol, 0.16 g) is dissolved in N-methylpyrrolidone (1.5 ml). Orthoformic acid trimethyl ester (0.0038 mol, 0.42 ml), copper chloride dihydrate solution (0.0013 mol, 0.22 g in 0.5 ml of NMP) and the appropriate ketone (0.0038 mol dissolved in 2 ml of NMP) are added to the solution. The reaction mixture is shaken for 4 hours at 70° C. The crude product is precipitated by the addition of 10 ml of 10% aqueous sodium sulfate solution, and the precipitate is then filtered off and washed with copious amounts of ethanol. Subsequent column chromatography (Nucleosil 5C18) using a mixture of acetonitrile and water yields the pure product.

APPLICATION EXAMPLES

Example 10

Sun Protection Lotion

|  | INCI-Name | % w/w |
|---|---|---|
| Part A | Glyceryl Stearate (and) PEG-100 Stearate | 5.00 |
|  | Stearyl Alcohol | 1.00 |
|  | Tripalmitin | 0.70 |
|  | Dimethicone | 2.00 |
|  | $C_{12-15}$ Alkyl Benzoate | 5.00 |
|  | Isopropyl Palmitate | 5.00 |
|  | Ethylhexyl Methoxycinnamate | 3.00 |
| Part B | Water | qs to 100 |
|  | Polysorbate 60 | 0.50 |
|  | Glycerin | 3.00 |
| Part C | Water | 10.00 |
|  | Compound of formula 101 or 102 or 103 or 104 or 105 or 106 | 8.00 |
| Part D | Phenoxyethanol (and) Methylparaben (and) Ethylparaben (and) Butylparaben (and) Propylparaben (and) Isobutylparaben | 0.70 |
|  | Steareth-10 Allyl Ether/Acrylates Copolymer | 1.50 |
| Part E | Water (and) Sodium Hydroxide | qs |
| Part F | Fragrance | qs |

This emulsion is easy to spread with good absorption properties.
Manufacturing Instruction:

Heat part A and B separately up to 75° C.; part C to 60° C. Afterwards pour part B into part A under stirring. Homogenize with an Ultra Turrax for 30 sec. at 11000 rpm and incorporate part C. Let cool down to 40° C. and add part D. At room temperature adjust the pH-value with Sodium Hydroxide between 6.30 and 6.70 and add part F.

Example 11

Sprayable Sunscreen Lotion

|  | INCI-Name | % w/w |
|---|---|---|
| Part A | Potassium Cetyl Phosphate | 0.20 |
|  | Isohexadecane | 7.00 |
|  | VP/Eicosene Copolymer | 1.50 |
|  | Di-$C_{12-13}$ Alkyl Tartrate | 6.00 |
|  | Ethylhexyl Triazone | 2.50 |
|  | $C_{12-15}$ Alkyl Benzoate | 4.50 |
| Part B | Water | qs to 100 |
|  | Sorbeth-30 | 2.00 |
|  | Sorbitan Stearate (and) Sucrose Cocoate | 4.00 |
|  | Titanium Dioxide (and) Alumina (and) Silica (and) Sodium Polyacrylate | 2.50 |
| Part C | Water | 30.00 |
|  | Compound of formula 101 or 102 or 103 or 104 on 105 or 106 | 12.00 |
| Part D | Phenoxyethanol (and) Methylparaben (and) Ethylparaben (and) Butylparaben (and) Propylparaben (and) Isobutylparaben | 0.70 |
| Part E | Water (and) Citric Acid | qs |

This emulsion contains a combination of insoluble UV-absorber. The choice of emollients provides quick absorption and smooth after skin feeling.
Manufacturing Instruction:

Heat part A and part B separately up to 80° C.; part C to 50° C. Pour part B into part A and homogenize with an Ultra Turrax for 1 minute by 11000 rpm. After cooling down to 50° C. add part C under continuous stirring. At 40° C. incorporate part D and homogenize again for 10 sec. by 11000 rpm. Adjust the pH with part E.

Example 12

Sunscreen Lotion, Water Resistant

|  | INCI-Name | % w/w |
|---|---|---|
| Part A | Cetearyl Alcohol (and) Dicetyl Phosphate (and) Ceteth-10 Phosphate | 4.00 |
|  | $C_{12-15}$ Alkyl Benzoate | 2.00 |
|  | Dicaprylyl Ether | 3.00 |
|  | Ethoxydiglycol Oleate | 2.00 |
|  | Stearic Acid | 1.00 |
|  | Ethylhexyl Methoxycinnamate | 3.00 |
|  | Sodium Acrylates Copolymer (and) Glycine Soja (and) PPG-1 Trideceth-6 | 0.30 |
|  | Squalane | 3.50 |
|  | VP/Eicosene Copolymer | 2.00 |
| Part B | Water | qs to 100 |
|  | Compound of formula 101 or 102 or 103 or 104 or 105 or 106 | 5.00 |
| Part C | Diazolidinyl Urea (and) Iodopropynyl Butylcarbamate | 0.15 |
|  | Propylene Glycol | 2.50 |
|  | Water | 10.00 |
| Part D | Cyclopentasiloxane (and) Dimethiconol | 2.00 |
|  | Ethoxydiglycol | 5.00 |
|  | Cyclopentasiloxane (and) Dimethicone/Vinyl Dimethicone Crosspolymer | 2.00 |
| Part E | Aqua (and) Sodium Hydroxide | qs |
| Part F | Fragrance | qs |

O/W emulsion with a soft touch and good rub in properties.
Manufacturing Instruction:

Heat part A and part B separately up to 75° C. Pour part B into part A under progressive stirring speed. Below 65° C.

add separately the ingredients of part D. Let cool down to 55° C. under moderate stirring and add part C. Less than 35° C. check and adjust the pH with Sodium Hydroxide and homogenize with an Ultra Turrax for 30 sec. at 11000 rpm. At room temperature add part F.

Example 13

| | INCI-Name | % w/w |
|---|---|---|
| Part A | Potassium Cetyl Phosphate | 2.00 |
| | Tricontanyl PVP | 1.00 |
| | Caprylic/Capric Triglyceride | 5.00 |
| | $C_{12-15}$ Alkyl Benzoate | 5.00 |
| | Cetearyl Isononanoate | 5.00 |
| | Glyceryl Stearate | 3.00 |
| | Cetyl Alcohol | 1.00 |
| | Dimethicone | 0.10 |
| | Ethylhexyl Methoxycinnamate | 5.00 |
| Part B | Water | qs to 100 |
| | Glycerin | 3.00 |
| Part C | Steareth-10 Allyl Ether/Acrylates Copolymer | 0.50 |
| Part D | Compound of formula 101 or 102 or 103 or 104 or 105 or 106 | 8.00 |
| Part E | Phenoxyethanol (and) Methylparaben (and) Ethylparaben (and) Butylparaben (and) Propylparaben (and) Isobutylparaben | 1.00 |
| Part F | Water (and) Sodium Hydroxide | qs to pH 7.00 |
| Part G | Fragrance | qs |

This emulsion is smooth and spreads easily. The choice of mainly light emollients gives the lotion a light and non-tacky skin feeling.

Manufacturing Instruction:

Heat part A and part B separately up to 80° C. Pour part B into part A under moderate stirring. Homogenize with an Ultra Turrax at 11000 rpm for 1 minute. Let cool down to 70° C. and add part C under stirring. Cool further down to 50° C. and incorporate TINOSORB® M very slowly. At 40° C. add part E. At room temperature adjust the pH with part F to 7.00 and add part G.

Example 14

O/W Emulsion Water Resistant

| | INCI-Name | % w/w |
|---|---|---|
| Part A | Cetearyl Alcohol (and) Dicetyl Phosphate (and) Ceteth-10 Phosphate | 4.00 |
| | $C_{12-15}$ Alkyl Benzoate | 2.00 |
| | Dicaprylyl Ether | 3.00 |
| | Ethoxydiglycol Oleate | 2.00 |
| | Stearic Acid | 1.00 |
| | Ethylhexyl Methoxycinnamate | 3.00 |
| | Sodium Acrylates Copolymer (and) Glycine Soja (and) PPG-1 Trideceth-6 | 0.30 |
| | Squalane | 3.50 |
| | VP/Eicosene Copolymer | 2.00 |
| Part B | Water | qs to 100 |
| | Compound of formula 101 or 102 or 103 or 104 on 105 or 106 | 5.00 |
| Part C | Diazolidinyl Urea (and) Iodopropynyl Butylcarbamate | 0.15 |
| | Propylene Glycol | 2.50 |
| | Water | 10.00 |

| | INCI-Name | % w/w |
|---|---|---|
| Part D | Cyclopentasiloxane (and) Dimethiconol | 2.00 |
| | Ethoxydiglycol | 5.00 |
| | Cyclopentasiloxane (and) Dimethicone/Vinyl Dimethicone Crosspolymer | 2.00 |
| Part E | Aqua (and) Sodium Hydroxide | qs |
| Part F | Fragrance | qs |

O/W emulsion with a soft touch and good rub in properties.

Manufacturing Instruction:

Heat part A and part B separately up to 75° C. Pour part B into part A under progressive stirring speed. Below 65° C. add separately the ingredients of part D. Let cool down to 55° C. under moderate stirring and add part C. Less than 35° C. check and adjust the pH with Sodium Hydroxide and homogenize with an Ultra Turrax for 30 sec. at 11,000 rpm. At room temperature add part F.

Example 14

Sun Protection Lotion, O/W Type

| | INCI-Name | % w/w |
|---|---|---|
| Part A | Potassium Cetyl Phosphate | 2.00 |
| | Tricontanyl PVP | 1.00 |
| | Caprylic/Capric Triglyceride | 5.00 |
| | $C_{12-1}5$ Alkyl Benzoate | 5.00 |
| | Cetearyl Isononanoate | 5.00 |
| | Glyceryl Stearate | 3.00 |
| | Cetyl Alcohol | 1.00 |
| | Dimethicone | 0.10 |
| | Ethylhexyl Methoxycinnamate | 5.00 |
| Part B | Water | qs to 100 |
| | Glycerin | 3.00 |
| Part C | Steareth-10 Allyl Ether/Acrylates Copolymer | 0.50 |
| Part D | Compound of formula 101 or 102 or 103 or 104 or 105 or 106 | 20.00 |
| Part E | Phenoxyethanol (and) Methylparaben (and) Ethylparaben (and) Butylparaben (and) Propylparaben (and) Isobutylparaben | 1.00 |
| Part F | Water (and) Sodium Hydroxide | qs to pH 7.00 |
| Part G | Fragrance | qs |

This emulsion is smooth and spreads easily.

Manufacturing Instruction:

Heat part A and part B separately up to 80° C. Pour part B into part A under moderate stirring. Homogenize with an Ultra Turrax at 11000 rpm for 1 minute. Let cool down to 70° C. and add part C under stirring. Cool further down to 50° C. and incorporate TINOSORB® M very slowly. At 40° C. add part E. At room temperature adjust the pH with part F to 7.00 and add part G.

What is claimed is:

1. A compound of formula (1)

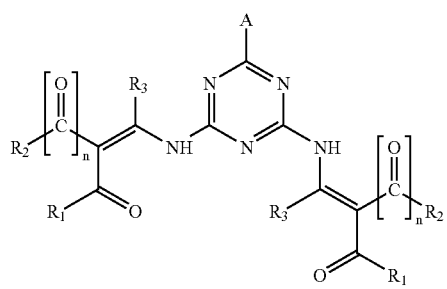

wherein $R_1$ is a $C_1$–$C_{18}$alkyl, $C_2$–$C_{18}$alkenyl, $C_6$–$C_{10}$aryl or $C_6$–$C_{10}$heteroaryl radical each unsubstituted or mono- or poly-substituted by hydroxy, $C_1$–$C_{18}$alkyl, $C_1$–$C_{18}$alkoxy, amino, $C_1$–$C_5$monoalkyl-amino or by di-$C_1$–$C_5$alkylamino; $C_5$–$C_7$cycloalkyl or $C_5$–$C_7$cycloalkenyl each unsubstituted or substituted by $C_1$–$C_5$alkyl; —OR'; or —NR'R";

$R_2$ is hydrogen; a $C_1$–$C_{18}$alkyl, $C_2$–$C_{18}$alkenyl, $C_6$–$C_{10}$aryl or $C_6$–$C_{10}$heteroaryl radical each unsubstituted or mono- or poly-substituted by hydroxy, $C_1$–$C_{18}$alkoxy, cyano, amino, $C_1$–$C_5$monoalkylamino or by di-$C_1$–$C_5$alkylamino; —OR'; or —NR'R"; or $R_1$ and $R_2$ together form a 5- to 7-membered carbocyclic or heterocyclic ring;

A is $C_1$–$C_5$alkyl; an unsubstituted or hydroxy-, $C_1$–$C_{18}$alkyl- or $C_1$–$C_{18}$alkoxy-substituted $C_6$–$C_{10}$aryl or heteroaryl radical; or a radical of formula (1a)

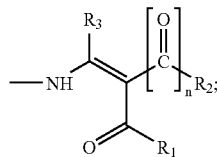

R' and R" are each independently of the other hydrogen; unsubstituted or mono- or poly-hydroxy-, halo-, $C_1$–$C_{18}$alkyl-, $C_1$–$C_{18}$alkoxy-, amino- or quaternary ammonium group-substituted $C_1$–$C_{18}$alkyl, $C_5$–$C_7$cycloalkyl or phenyl;

$R_3$ is hydrogen; or $C_1$–$C_6$alkyl; and n is 0 or 1.

2. A compound according to claim 1, wherein $R_1$ and $R_2$ are each independently of the other $C_1$–$C_{18}$alkyl or phenyl each unsubstituted or substituted by $C_1$–$C_5$alkyl, hydroxy or by $C_1$–$C_5$alkoxy; —OR'; or —NR'R"; or $R_1$ and $R_2$ together form a 5- to 7-membered carbocyclic or heterocyclic ring.

3. A compound according to claim 1, wherein $R_1$ is $C_1$–$C_5$alkyl; $C_1$–$C_5$alkoxy; or unsubstituted or $C_1$–$C_5$alkyl-, hydroxy- or $C_1$–$C_5$alkoxy-substituted phenyl.

4. A compound according to claim 1, wherein $R_2$ is hydrogen; $C_1$–$C_5$alkyl; $C_1$–$C_5$alkoxy; unsubstituted or hydroxy-, $C_1$–$C_5$alkyl- or $C_1$–$C_5$-alkoxy-substituted phenyl; and n is 1.

5. A compound according to claim 1, wherein $R_1$ and $R_2$ together are a —$(CH_2)_{2-5}$— radical that is not further substituted or is substituted by one or more $C_1$–$C_5$alkyl groups and is uninterrupted or interrupted by one or two —O— and/or —NH— groups and/or

6. A compound according to claim 5, wherein $R_1$ and $R_2$ together are a

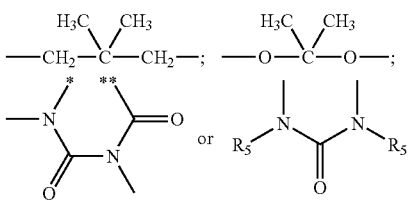

radical; and $R_5$ is hydrogen; or $C_1$–$C_5$alkyl.

7. A compound according to claim 1, wherein

A is amino; phenyl; or $C_1$–$C_5$alkoxyphenyl.

8. A compound according to claim 1, wherein $R_3$ is hydrogen.

9. A method for the protection of human and animal hair and skin against the damaging effect of UV radiation, which comprises contacting said hair or skin with an effective protective amount of a triazine derivative of formula (1) according to claim 1.

10. A method according to claim 9, wherein the triazine derivative of formula (1) is present in micronised form.

11. A cosmetic preparation comprising at least one compound of formula (1) according to claim 1 together with a cosmetically tolerable carrier or adjuvant.

12. A preparation according to claim 11 that comprises further UV protective substances.

* * * * *